United States Patent [19]

Okamoto et al.

[11] Patent Number: 4,873,253
[45] Date of Patent: Oct. 10, 1989

[54] PHENYLALANINE DERIVATIVE AND PROTEINASE INHIBITOR

[75] Inventors: Shosuke Okamoto, 15-18, Asahigaoka 3-chome, Tarumi-ku, Kobe-shi, Hyogo; Yoshio Okada, Akashi; Akiko Okunomiya, Kobe; Taketoshi Naito, Ohta; Yoshio Kimura, Ohta; Morihiko Yamada, Ohta; Norio Ohno, Ohta; Yasuhiro Katsuura, Ohta; Hiroshi Nojima, Ohta; Takashi Shishikura, Ohta, all of Japan

[73] Assignees: Shosuke Okamoto, Hyogo; Showa Denko Kabushiki Kaisha, Tokyo, both of Japan

[21] Appl. No.: 31,738

[22] Filed: Mar. 30, 1987

[51] Int. Cl.⁴ ...................... A61K 31/44; C07C 79/46; C07D 401/00; C07D 233/66
[52] U.S. Cl. .................... 514/352; 564/157; 560/21; 560/22; 560/34; 560/35; 560/39; 560/41; 562/435; 562/437; 562/439; 562/440; 562/448; 562/450; 260/998.2; 546/256; 546/261; 546/264; 546/266; 546/267; 546/276; 546/278; 546/280; 546/194; 546/209; 546/210; 546/187; 546/188; 546/190; 544/82; 544/78; 544/86; 544/121; 544/122; 544/130; 544/139; 544/133; 544/132; 544/131; 544/296; 544/295; 544/316; 544/331; 544/332; 544/357; 544/360; 544/364; 544/370; 544/369; 544/366; 548/251; 548/337; 548/187; 548/195; 514/231.8; 514/232.2; 514/235.8; 514/236.2; 514/236.8; 514/237.2; 514/237.8; 514/255; 514/269; 514/272; 514/274; 514/275; 514/316; 514/317; 514/326; 514/327; 514/329; 514/332; 514/333; 514/335; 514/340; 514/341; 514/342; 514/345; 514/349; 514/357; 514/359; 514/369; 514/370; 514/371; 514/542; 514/570; 514/616
[58] Field of Search ............... 564/155, 161, 163, 164, 564/157, ; 546/231, 233, 234, 332, 336, 337, 256, 261, 264, 266, 267, 276, 278, 280, 194, 209, 210, 187, 188, 190; 514/331, 357, 482, 483, 485, 231.8, 232.2, 235.8, 236.2, 236.8, 237.2, 237.8, 255, 269, 272, 274, 275, 316, 317, 326, 327, 329, 332, 333, 335, 340, 341, 342, 345, 349, 352, 357, 359, 369, 370, 371, 542, 570, 616; 560/21, 22, 34, 35, 39, 41; 562/435, 437, 439, 440, 448, 450; 260/998.2; 544/82, 78, 86, 121, 122, 130, 139, 133, 132, 131, 296, 295, 316, 331, 332, 357, 360, 364, 370, 369, 366; 548/251, 537, 187, 195

[56] References Cited

U.S. PATENT DOCUMENTS 4,025,644  5/1977  Miki et al. .......................... 564/157
4,261,919  4/1985  Knowles et al. .................... 564/157

FOREIGN PATENT DOCUMENTS 0048433  3/1982  European Pat. Off. .......... 564/157
0183271  7/1983  European Pat. Off. .......... 564/157
0183271  4/1986  European Pat. Off. .......... 564/157

2146458  3/1973  France ............................ 564/157
0042356  7/1984  Japan ............................ 564/157

OTHER PUBLICATIONS

CA vol. 101, No. 1, Jul. 2, 1984.
CA 82-27789u, FEBS Lett., 43, pp. 281 (1974).
CA 103-209699g, Il. Farmco. Ed. Sc., 40, p. 717 (1985).
CA 49-12707g, Antibiotics & Chemotherapy, 5, p. 152 (1955).
CA 101-76212p, Pharmazie, 39H1, p. 68 (1984).
CA 53-9299g, J. Biochem. (Tokyo), 46, p. 19 (1959).
CA 93-101418t, Biochem. Biophys. Res. Comm., 94, p. 284 (1980).
CA 84-160982j, Bioklimiya, 41, p. 294 (1976).

Primary Examiner—Mary C. Lee
Assistant Examiner—Robert C. Whittenbaugh
Attorney, Agent, or Firm—Sughrue, Mion, Zinn, Macpeak & Seas

[57] ABSTRACT

A phenylalanine derivative having the formula (I):

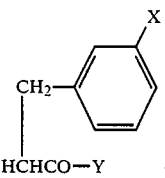

wherein
A represents (a) $H_2N-$, (b) $H_2N-\underset{\underset{NH}{\|}}{C}-$, or (c) $H_2N-\underset{\underset{NH}{\|}}{C}-NH-$;

B represents

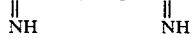

or (c) $-(CH_2)_{\overline{n}}$, wherein m is 0, 1, or 2 and n is 3, 4, or 5;
X represents (a) hydroxy, (b) nitro, (c) amino, (d) phenoxy which may be substituted with (i) halogen or (ii) nitro, (e) $c_1$–$C_4$ alkyloxy which may be substituted wit (i) phenyl or (ii) benzoyl, (f) benzoyl, (g) pyridyloxy which may be substituted with (i) halogen or (ii) nitro, or (h) $c_1$–$C_4$ alkyl which may by substituted with halogen;
Y represents

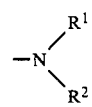

(Abstract continued on next page.)

or —OR$^3$ wherein

R$^1$ R$^2$ are independently (a) hydrogen, (b) phenyl which may be substituted with (i) benzoyl, (ii) C$_1$-C$_4$ alkylcarbonyl, (iii) C$_1$-C$_4$ alkyl which may be further substituted with C$_1$-C$_4$ alkoxycarbonyl or hydroxycarbonyl, (iv) C$_2$-C$_5$ alkenyl which may be further substituted with hydroxycarbonyl or C$_1$-C$_4$ alkoxycarbonyl, (v) C$_1$-C$_4$ alkoxycarbonyl, or (vi) amidino, (c) pyridyl which may be substituted with halogen or carboxyl (d) imidazolyl, (e) pyrimidyl, (f) tetrazolyl, (g) thiazolyl which may be substituted with C$_1$-C$_4$ alkyl which may be further substituted with C$_1$-C$_4$ alkoxycarbonyl, (h) C$_1$-C$_6$ alkyl which may be substituted with C$_1$-C$_4$ alkoxy, C$_1$-C$_4$ alkoxycarbonyl, phenyl, or benzoyl, (i) C$_5$-C$_7$ cycloalkyl which may be substituted with C$_1$-C$_4$ alkoxycarbonyl or (j) R$^1$ and R$^2$ may form, with the nitrogen atom attached thereto, (i) pyperazyl which may be substituted on the nitrogen atom with C$_1$-C$_4$ alkyl which may be further substituted with phenyl, (ii) piperidino which may be substituted with carboxyl or C$_1$-C$_4$ alkoxycarbonyl, (iii) pyrrolidyl which may be substituted with C$_1$-C$_4$ alkoxycarbonyl, or (iv) morpholyl; and R$^3$ represents (a) hydrogen, (b) C$_1$-C$_6$ alkyl which may be substituted with (i) C$_1$-C$_4$ alkoxy, (ii) pehnyl, or (iii) pyridyl, or (c) pyridyl; or a pharmaceutically acceptable acid salt thereof.

This phenylalanine derivative is effective as a proteinase.

20 Claims, No Drawings

PHENYLALANINE DERIVATIVE AND PROTEINASE INHIBITOR

BACKGROUND OF THE INVENTION

1. Field of the Invention

The present invention relates to a novel phenylalanine derivative, more particularly to a phenylalanine derivative having a proteinase inhibition activity or a pharmaceutically acceptable salt thereof. The present invention also relates to a proteinase inhibitor containing the same as the effective ingredient.

2. Description of the Related Art

Various proteases exist in the body, as is well known. For example, the serine proteases of kallikrein, trypsin, plasmin, urokinase, etc. are known.

Of these, kallikrein is widely distributed in the blood and in various viscera and glands, and normally exists as its precursor prekallikrein and is activated by Hagenman factor or other proteases. The normal actions of kallikrein in the body are (1) lowering of the blood pressure by kallikrein-kinin system, (2) activation of the fibrinolysis by the formation of plasmin from plasminogen, (3) contribution to intrinsic blood coagulation, (4) activation of the complementary systems, and (5) improvement of local circulation in the viscera or glands. On the other hand, abnormal activation of kallikrein, in local areas, is accompanied by activation of the coagulation and fibrinolysis and the resultant disorder of local circulation and disseminated intravascular coagulation, causing tissue obstruction. This is believed to be a cause of inflammation, ulcer, etc. and of induction of allergic reactions due to activation of the complementary system.

Therefore, strong inhibitors of kallikrein are useful for control of blood pressure, treatment of inflammation, acute pancreatitis and pancreatic necrosis, ulcer, and allergies and for immunoregulators.

Trypsin is inherently present in the pancreas as the trypsinogen, but alcohol, cholelith, injury, etc. lead to its activation in the pancreas, resulting self-digestion of the pancreas and clinical symptoms of pancreatitus. Further, when trypsin is injected retrogradly to the pancreas in rats, severe pancreatitis is observed. It has been confirmed that this is curable by a trypsin inhibitor.

Therefore, strong inhibitors of trypsin are useful for the clinical treatment of pancreatitis.

For some time, research has been underway to develop protease inhibitors having such action. Among the same, as a drug having pharmacological properties relatively resembling the present invention, there is known, as shown in Table 3, the protease inhibitor, aprotinin, which is polypeptides obtained from ox lungs. When aprotinin is administered to humans, it becomes itself an antigen and thus results in side effects such as allergic reactions. Further, it cannot be used over long periods or repeatedly. Further, in recent years, FUT-175 as shown in Table 3, which has become known as a broad protease inhibitor, has been used for the improvement of acute pancreatitis. The broad inhibition spectrum, the short half life in vivo, the large hypotensive action, and the small LD$_{50}$ value mean that full supervision is required in clinical use, and this places a large burden on both the patient and the doctor. The present invention has as its object the development of a compound which sufficiently resolves the problems of the prior art, with high selective inhibition action, low molecular weight, long half life in vivo, and a large LD$_{50}$ value and a protease inhibitor containing the same as the effective ingredient.

SUMMARY OF THE INVENTION

Accordingly, the objects of the present invention are to eliminate the above-mentioned disadvantages of the prior art and to provide a compound having a satisfactory inhibition activity in practical application and having satisfactory inhibition activities against various proteinases, and a proteinase inhibitor containing the compound as the effective ingredient.

Other objects and advantages of the present invention will be apparent from the following description.

In accordance with the present invention, there is provided a phenylalanine derivative having the formula (I):

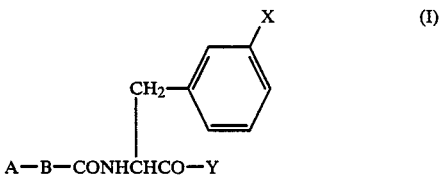

wherein
A represents

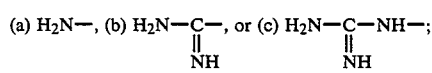

B represents

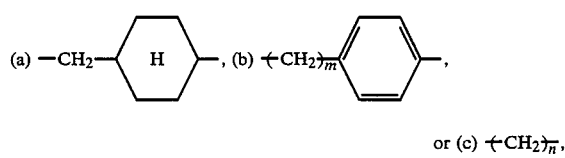

wherein m is 0, 1, or 2 and n is 3, 4, or 5;

X represents (a) hydroxy, (b) nitro, (c) amino, (d) phenoxy which may be substituted with (i) halogen or (ii) nitro, (e) $C_1$–$C_4$ alkyloxy which may be substituted with (i) phenyl or (ii) benzoyl, (f) benzoyl, (g) pyridyloxy which may be substituted with (i) halogen or (ii) nitro, or (h) $C_1$–$C_4$ alkyl which may be substituted with halogen;

Y represents

or —OR$^3$ wherein
R$^1$ and R$^2$ are independently (a) hydrogen, (b) phenyl which may be substituted with (i) benzoyl, (ii) $C_1$–$C_4$ alkylcarbonyl, (iii) $C_1$–$C_4$ alkyl which may be further substituted with $C_1$–$C_4$ alkoxycarbonyl or hydroxycarbonyl, (iv) $C_2$–$C_5$ alkenyl which may be further substituted with hydroxycarbonyl or $C_1$–$C_4$ alkoxycarbonyl, (v) $C_1$–$C_4$ alkoxycarbonyl, or (vi) amidino, (c) pyridyl which may be substituted with halogen or carboxyl (d) imidazolyl, (e) pyrimidyl, (f) tetrazolyl, (g) thiazolyl which may be substituted with $C_1$-$C_4$ alkyl which may be further substituted with $C_1$-$C_4$ alkoxycarbonyl, (h) $C_1$-$C_6$ alkyl which may be substituted with $C_1$-$C_4$ alkoxy, $C_1$-$C_4$ alkoxycarbonyl, phenyl, or benzoyl, (i) $C_5$-$C_7$ cycloalkyl which may be substituted with $C_1$-$C_4$ alkoxycarbonyl or (j) $R^1$ and $R^2$ may form, with the nitrogen atom attached thereto, (i) pyperazyl which may be substituted on the nitrogen atom with $C_1$-$C_4$ alkyl which may be further substituted with phenyl, (ii) piperidino which may be substituted with carboxyl or $C_1$-$C_4$ alkoxycarbonyl, (iii) pyrrolidyl which may be substituted with $C_1$-$C_4$ alkoxycarbonyl, or (iv) morpholyl; and $R^3$ represents (a) hydrogen, (b) $C_1$-$C_6$ alkyl which may be substituted with (i) $C_1$-$C_4$ alkoxy, (ii) phenyl, or (iii) pyridyl, or (c) pyridyl; or a pharmaceutically acceptable acid salt thereof.

Examples of the pharmaceutically acceptable salts are inorganic acid-salts such as hydrochloride, hydrobromide, hydroiodide, sulfate, nitrate, phosphate, etc.; organic acid salts such as oxalate, succinate, glycolate, malate, citrate, maleate, lactate, benzenesulfonate, toluenesulfonate, methanesulfonate, etc.

In accordance with the present invention, there is also provided a proteinase inhibitor comprising the phenylalanine derivative of the above formula (I) or a pharmaceutically acceptable salt thereof as the active ingredient.

DESCRIPTION OF THE PREFERRED EMBODIMENTS

The compounds according to the present invention have phenylalanine as a basic skeleton as shown in the general formula (I) and have a characteristic structure in which amino, amidino, or guanidino group (i.e., group A) is attached to the N-terminal of the amino group of the phenylalanine by a peptide linkage via the hydrocarbon group (i.e., group B) having certain size. The preferable combination of the groups A and B (i.e., A-B) are as follows.

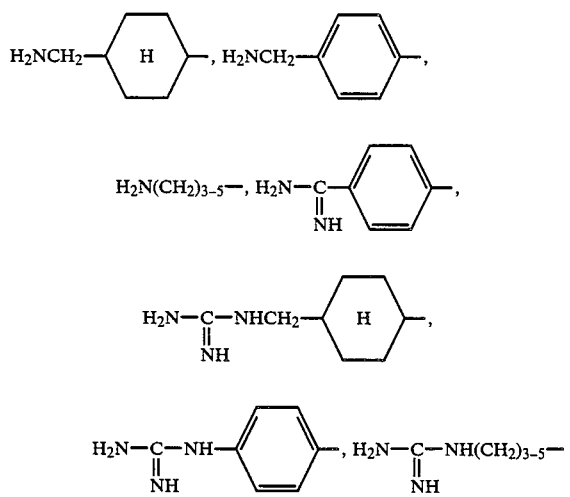

Of these combinations, the following is especially preferable.

On the other hand, to the terminal carbon of the carboxyl group of phenylalanine, various substituents are bonded via the peptide linkage, but optionally, carboxyl group per se or ester form is bonded. Furthermore, specified substituents (e.g., group X) are introduced at the 3-position (i.e., meta position) for the benzene ring of the phenylalanine.

Among various substituents in the X and Y groups, the followings are especially preferable:

X: nitro, phenoxy which may be substituted with halogen or nitro; $C_1$ alkyloxy which may be substituted with benzoyl; benzoyl; pyridyloxy which may be substituted with halogen or nitro;

Y: NHR or $OR_4$ wherein R is (a) phenyl which may be substituted with (i) benzoyl, (ii) $C_1$-$C_4$ alkylocarbonyl, (iii) $C_1$-$C_3$ alkyl which may be further substituted with $C_1$-$C_2$ alkoxycarbonyl, (b) pyridyl which may be substituted with halogen or carboxyl (c) tetrazolyl, (d) thiazolyl which may be substituted with $C_1$-$C_3$ alkyl which may be further substituted with $C_1$-$C_2$ alkoxycarbonyl, (e) $C_1$-$C_4$ alkyl which may be substituted with $C_1$-$C_2$ alkoxy, $C_1$-$C_2$ alkoxycarbonyl, or (f) cyclohexyl which may be substituted with $C_1$-$C_2$ alkoxycarbonyl;

and $R_4$ is $C_1$-$C_4$ alkyl which may be substituted with $C_1$-$C_2$ alkoxy, or pyridyl, or pyridyl;

and a pharmaceutically acceptable salt thereof.

Typical examples of the compound represented by the above formula are listed in Table 1.

The compounds listed in the Table are numbered, respectively, and in the following description, the individual compounds are designated in terms of said compound Nos. for the purpose of convenience.

For the compounds indicated as (L), this means that their carbons are L-form; and, in the compounds indicated as (D), this means that its carbon is D-form. In the physical properties shown in Table 1, NMR represents a nuclear magnetic resonance spectrum indicated by $\delta$ (i.e., delta) (ppm) representing the chemical shifts. The determination was carried out by using as a solvent $CDCl_3$ (i.e., chloroform-$d_1$), or $CD_3OD$ (i.e., methanol-$d_4$), and by using as an internal standard TMS (i.e., tetramethylsilane). In the parenthesis after the $\delta$ number, the number of the hydrogen atom and the symbols s, d, t, q, m, and broad, thereafter, denote singlet, doublet, triplet, quartet, multiplet, and broad absorbance, respectively. The absorbance based on the solvent is not shown in the Table 1.

IR represents an infrared absorption spectrum in which a potassium bromide tablet is used in the determination unless otherwise noted. When a solution is used in the determination, the kind of solvent is listed in parenthesis. The number listed in the Table represents a wave number in units of $cm^{-1}$, and only the main absorption peaks are listed in the Table 1.

MS represents a mass spectrum, and the results are shown as M/e (i.e., the mass of the cation fragment divided by the charge) of the main peaks.

TABLE 1

| No. | Compound | Physical Properties |
|---|---|---|
| 1 | H₂NCH₂—[cyclohexyl]···CONHCHCONH—[phenyl]—CH₃·HCl, with CH₂—[3-phenoxyphenyl] side chain | MS: M/e 485,379,351,329, 223,212,140,107, |
| 2 | H₂NCH₂—[cyclohexyl]···CONHCHCONH—[phenyl]—C(O)—CH₃·HCl, with CH₂—[3-phenoxyphenyl] side chain | NMR: CD₃OD,TMS δ: 0.80–2.32(10H,m) 2.50(3H,s) 2.78(2H,d) 2.90–3.30(2H,m) 4.70–4.82(1H,m) 6.76–7.96(13H,m) |
| 3 | H₂NCH₂—[cyclohexyl]···CONHCHCONH—[phenyl(CO₂C₂H₅)]·HCl, with CH₂—[3-phenoxyphenyl] side chain | MS: M/e 543,387,351,223, 212,165,140,112, |
| 4 | H₂NCH₂—[cyclohexyl]···CONHCHCONH—[phenyl(CO₂C₂H₅)]·HCl, with CH₂—[3-phenoxyphenyl] side chain | IR: 2930,1720,1690,1580, 1480,1450,1250,1080, 750 |
| 5 | H₂NCH₂—[cyclohexyl]···CONHCHCONH—[phenyl]—C(=NH)(NH₂)·2HCl, with CH₂—[3-phenoxyphenyl] side chain | MS: M/e 496,478,394,379, 360,223,212,183, 135,119,91 |
| 6 | H₂NCH₂—[cyclohexyl]···CONHCHCONH—[pyridyl]·2HCl, with CH₂—[3-phenoxyphenyl] side chain | IR: 3325,3250,1660,1645, 1610,1570 |

TABLE 1-continued
| No. | Compound | Physical Properties |
|---|---|---|
| 7 | 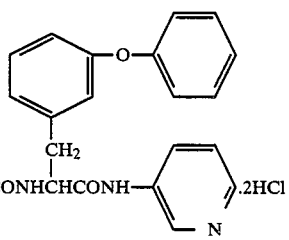 | IR: 3400,2940,2860,1650, 1555,1495,1460,1250, 1212 |
| 8 | 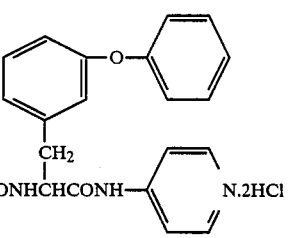 | NMR: $CD_3OD$,TMS δ: 0.92–2.35(10H,m) 2.80(2H,d) 2.95–3.33(2H,m) 4.70–4.84(1H,m) 6.86–7.36(9H,m) 8.14(2H,d) 8.60(2H,d) |
| 9 | 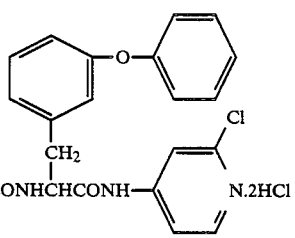 | NMR: $CD_3OD$,TMS δ: 0.88–2.40(10H,m) 2.82(2H,d) 2.92–3.30(2H,m) 4.70–4.82(1H,m) 6.78–7.36(9H,m) 7.68–7.75(1H,m) 8.03(1H,d) 8.35–8.39(1H,m) |
| 10 | 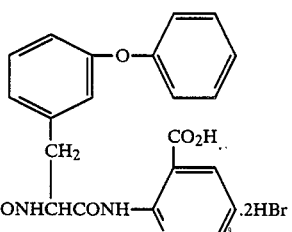 | IR: 3400,2930,1730,1640, 1480,1250,1210,1020, 770 |
| 11 | 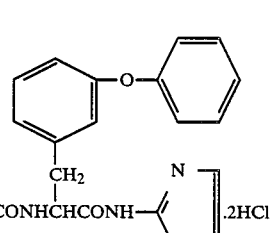 | NMR: $CD_3OD$,TMS δ: 0.90–2.36(10H,m) 2.79(2H,d) 2.96–3.30(2H,m) 4.70–4.80(1H,m) 6.80–7.36(11H,m) |
| 12 | 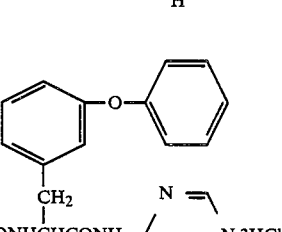 | NMR: $CD_3OD$,TMS δ: 0.84–2.28(10H,m) 2.77(2H,d) 2.84–3.20(2H,m) 4.52–4.72(1H,m) 6.66–8.60(12H,m) |

TABLE 1-continued
| No. | Compound | Physical Properties | |
|---|---|---|---|
| 13 | 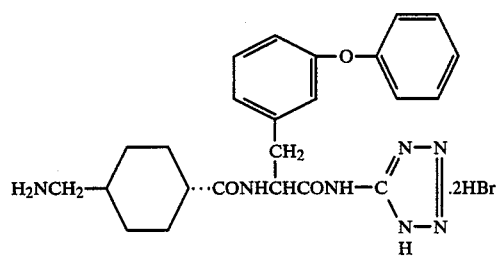 | IR:<br>3400,2930,1680,1620,<br>1490,1450,1240 | |
| 14 | 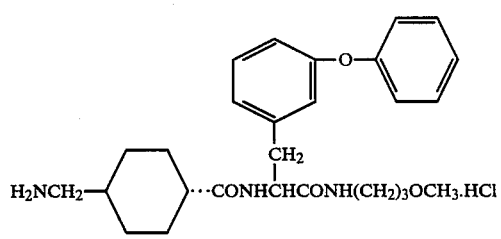 | IR:<br>3400,3280,2940,1660,<br>1640,1582,1555,1490,<br>1445,1250,1215 | NMR:<br>CD$_3$OD,TMS<br>δ: 0.88–2.28(12H,m)<br>2.75–3.36(8H,m)<br>3.28(3H,s)<br>4.48–4.56(1H,m)<br>6.78–7.38(9H,m) |
| 15 | 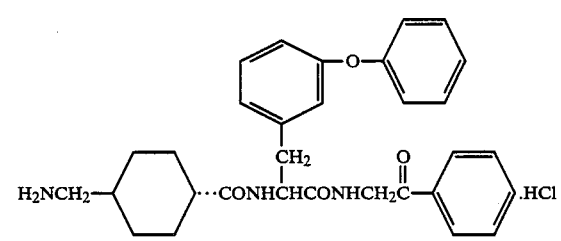 | IR:<br>3400,2930,1690,1640,<br>1480,1250,1210 | |
| 16 | 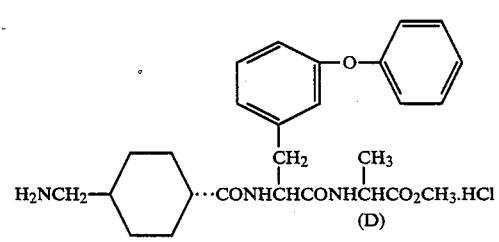 | IR:<br>3280,2940,2860,1750,<br>1660,1643,1545,1492<br>1450,1250,1215 | |
| 17 | 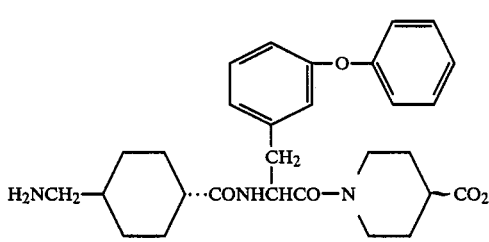 | IR:<br>3400,2930,1620,1480,<br>1250,1210,690 | |
| 18 | 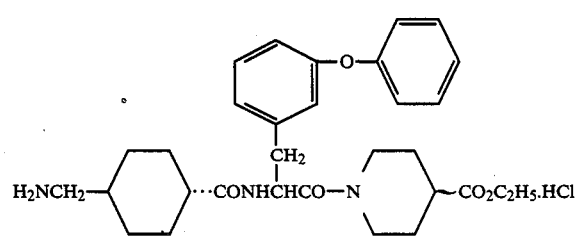 | IR:<br>2930,1730,1620,1480,<br>1450,1250,1210,1035,<br>690 | |

TABLE 1-continued
| No. | Compound | Physical Properties | |
|---|---|---|---|
| 19 | 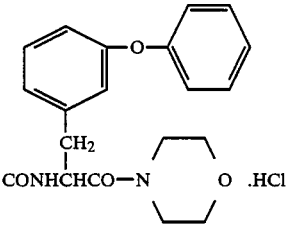 | IR: 2930,2860,1640,1630, 1530,1490,1445,1245, 1210,1110 | |
| 20 | 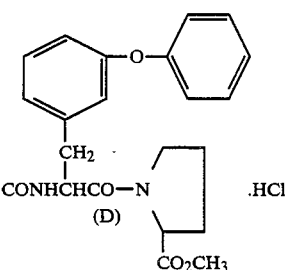 | IR: 3420,3280,2940,2860, 1750,1640,1592,1535, 1490,1450,1250,1215 | |
| 21 | 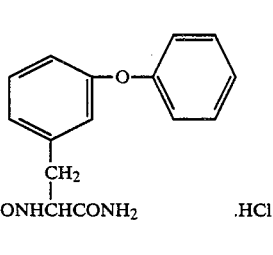 | IR: 2930,1660,1480,1250, 1210 | |
| 22 | 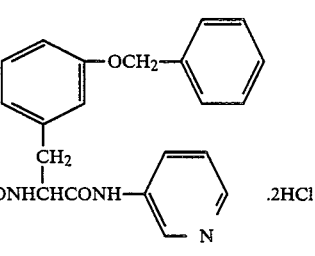 | IR: 3050,2925,2850,1650, 1550,1455 | NMR: CD$_3$OD,TMS δ: 0.90–2.37(10H,m) 2.78(2H,d) 2.92–3.30(2H,m) 4.72–4.80(1H,m) 5.03(2H,s) 6.80–7.48(9H,m) 7.97–8.08(1H,m) 8.44–8.58(1H,m) 9.36(1H,s) |
| 23 | 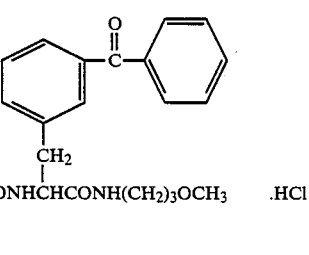 | IR: 3300,2940,2860,1660, 1642,1540,1450,1280, 1120 | NMR: CD$_3$OD,TMS δ: 0.90–2.18(12H,m) 2.76(2H,d) 2.88–3.30(6H,m) 3.26(3H,s) 4.52–4.64(1H,m) 7.40–7.80(10H,m) |
| 24 | 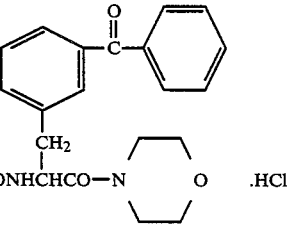 | IR: 1660,1645,1600,1530, 1450,1280,1110 | |

TABLE 1-continued
| No. | Compound | Physical Properties |
|---|---|---|
| 25 | 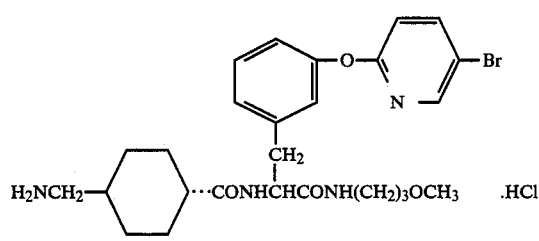 | IR: 2940,2860,1640,1580, 1525,1450,1280,1110<br>NMR: CD$_3$OD,TMS<br>δ: 0.88–2.18(12H,m)<br>2.77(2H,d)<br>2.85–3.30(6H,m)<br>3.28(3H,s)<br>4.50–4.61(1H,m)<br>6.90–7.40(5H,m)<br>8.02–8.08(1H,m)<br>8.26–8.30(1H,m) |
| 26 | 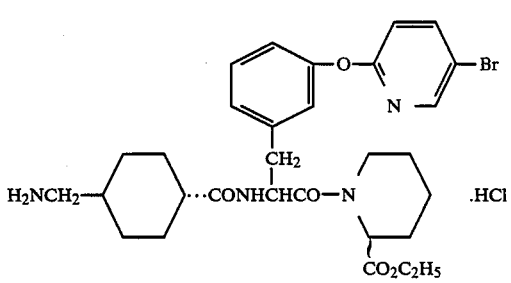 | IR: 3400,3275,2940,2860, 1740,1640,1580,1530, 1455,1270,1240,1210 |
| 27 | 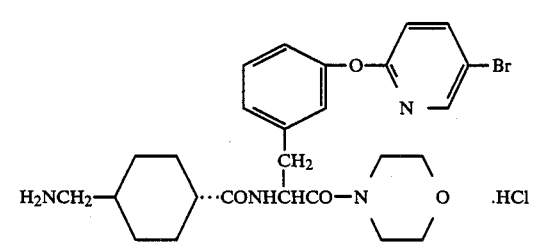 | IR: 3410,3270,2940,2860, 1640,1580,1530,1460, 1265,1240 |
| 28 | 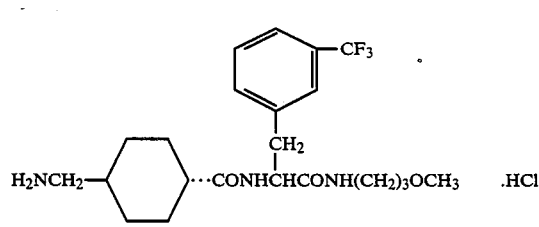 | IR: 3250,3100,2940,1660, 1620,1575,1335,1120<br>NMR: CD$_3$OD,TMS<br>δ: 0.80–2.30(12H,m)<br>2.77(2H,d)<br>2.90–3.30(6H,m)<br>3.31(3H,s)<br>4.55–4.62(1H,m)<br>7.44–7.56(4H,m) |
| 29 | 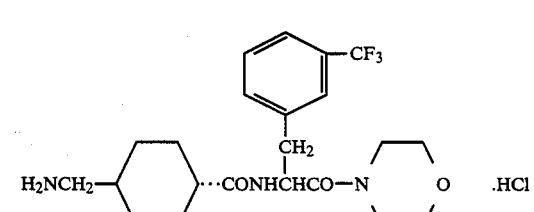 | IR; 1650,1540,1455,1330 |
| 30 | 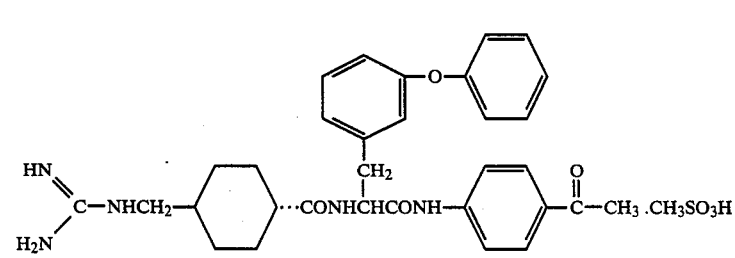 | IR: 3320,2930,1640,1600, 1540,1270,1210,1170, 1040 |

TABLE 1-continued
| No. | Compound | Physical Properties |
|---|---|---|
| 31 | 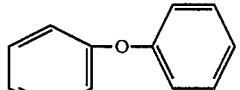 | IR: 3400,1730,1630,1480, 1450,1200,1040 |
| 32 | 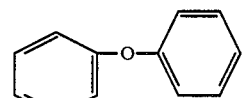 | IR: 3380,1680,1600,1535, 1480,1400,1250,1200, 1170,1040 |
| 33 | 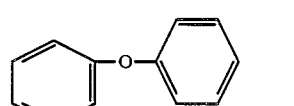 | MS: M/e 566,162  IR: 3400,3200,1715,1680, 1640,1600,1485,1445, 1285,1245,1210,1040, 755,695 |
| 34 | 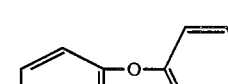 | MS: M/e 558,373,162  IR: 3380,3180,2980,2930, 1730,1630,1580,1485, 1445,1310,1250,1210, 1040,780,695 |
| 35 | 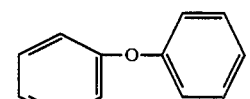 | IR: 3425,3200,2850,1680, 1630,1580,1490,1250, 1210,1040,780,690 |
| 36 | 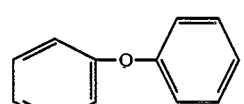 | NMR: CD$_3$OD,TMS δ: 3.04–3.72(5H,m) 4.04–4.30(1H,m) 4.60–5.00(1H,broad) 6.76–8.00(17H,m) |

TABLE 1-continued

| No. | Compound | Physical Properties | |
|---|---|---|---|
| 37 | (guanidino-phenyl)–NH–C(=NH)–NH–C₆H₄–CONH–CH(CH₂–C₆H₄–O–C₆H₅)–CONH–C₆H₄–CH=CH–CO₂H ·HCl | IR: 3420,3030,1680,1635, 1595,1530,1485,1245, 1210,1185,980,830, 755,690 | |
| 38 | H₂NCH₂–(cyclohexyl)–CONH–CH(CH₂–C₆H₄–O–C₆H₅)–CONH–C(=S)–N=C(CH₂CO₂C₂H₅) ·HCl | IR: 2940,2860,1738,1665, 1655,1660,1585,1555, 1520,1490,1250,1215 | NMR: CD₃OD,TMS δ: 0.90–2.35(10H,m) 1.27(3H,t) 2.78(2H,d) 2.95–3.30(2H,m) 3.88(2H,s) 4.18(2H,q) 4.78–4.90(1H,m) 6.79–7.36(10H,m) |
| 39 | H₂NCH₂–(cyclohexyl)–CONH–CH(CH₂–C₆H₄–CO–C₆H₅)–CONH–C(=S)–N=C(CH₂CO₂C₂H₅) ·HCl | IR: 3320,2940,2860,1725, 1700,1670,1650,1595, 1560,1510,1310,1285 | NMR: CD₃OD,TMS δ: 0.90–2.35(10H,m) 1.26(3H,t) 2.78(2H,d) 3.02–3.40(2H,m) 3.84(2H,s) 4.18(2H,q) 4.80–4.90(1H,m) 7.18(1H,s) 7.40–7.76(9H,m) |
| 40 | H₂NCH₂–(cyclohexyl)–CONH–CH(CH₂–C₆H₄–CO–C₆H₅)–CONH–(cyclohexyl-CO₂C₂H₅) ·HCl | IR: 3300,2940,2860,1735, 1665,1645,1535,1315, 1280 | NMR: CD₃OD,TMS δ: 0.85–2.45(22H,m) 2.76(2H,d) 2.90–3.20(2H,m) 3.50–3.64(1H,m) 4.00–4.15(2H,m) 4.50–4.62(1H,m) 7.40–7.76(9H,m) |
| 41 | H₂NCH₂–(cyclohexyl)–CONH–CH(CH₂–C₆H₄–CO–C₆H₅)–CONH–C₆H₄–CO–C₆H₅ ·HCl | IR: 2940,2860,1660,1655, 1600,1530,1315,1280 | |
| 42 | H₂NCH₂–C₆H₄–CONH–CH(CH₂–C₆H₄–O–C₆H₅)–CONH–C₆H₄–CH=CH–CO₂CH₃ ·HCl | IR: 3420,3030,2950,1700, 1630,1595,1535,1510, 1485,1245,1210,1170, 980,945,830,750, 690 | |

TABLE 1-continued

| No. | Compound | Physical Properties |
|---|---|---|
| 43 | (structure: 4-guanidinophenyl–CONHCH(CH₂-3-phenoxyphenyl)CONH–4-(CH₂CO₂C₂H₅)phenyl·HCl) | IR: 3300,3250,3200,3000, 1740,1680,1640,1600, 1540,1490,1420,1250, 1210,1160,1020,950, 840,760,690 |
| 44 | (structure: 4-(H₂NCH₂)cyclohexyl–CONHCH(CH₂-3-nitrophenyl)CONH–4-benzoylphenyl·HCl) | IR: 3420,2940,1640,1600, 1520,1340,1270,1170, 700 |
| 45 | (structure: 4-(H₂NCH₂)phenyl–CONHCH(CH₂-3-phenoxyphenyl)CONH(CH₂)₂CO₂C₂H₅·HCl) | IR: 3300,1740,1660,1645, 1545,1495,1250,1215     NMR: CD₃OD,TMS δ: 1.22(3H,t) 2.42–2.51(2H,m) 2.95–3.50(6H,m) 4.10(2H,q) 4.17(2H,s) 4.72–4.81(1H,m) 6.76–7.32(9H,m) 7.52(2H,d) |
| 46 | (structure: 4-(H₂NCH₂)phenyl–CONHCH(CH₂-3-phenoxyphenyl)CO–N(piperazine)N–CH₂-phenyl·2HCl) | IR: 1650,1585,1490,1250, 1215 |
| 47 | (structure: 4-(H₂NCH₂)phenyl–CONHCH(CH₂-3-benzoylphenyl)CONH-biphenyl·HCl) | IR: 3300,1660,1640,1540, 1505,1315,1282 |
| 48 | (structure: 4-(H₂NCH₂)cyclohexyl–CONHCH(CH₂-3-(5-nitropyridin-2-yloxy)phenyl)CONH–4-(COCH₃)phenyl·HCl) | IR: 2935,2860,1680,1650, 1600,1540,1520,1345, 1265,1258     NMR: CD₃OD,TMS δ: 0.88–2.32(10H,m) 2.56(3H,s) 2.76–2.82(2H,m) 2.92–3.30(2H,m) 4.70–4.80(1H,m) 6.99–7.42(5H,m) 6.62(2H,d) 6.90(2H,d) 8.40–8.48(1H,m) 8.72–8.76(1H,m) |

TABLE 1-continued

| No. | Compound | Physical Properties |
|---|---|---|
| 49 | H₂NCH₂—[cyclohexyl]···CONHCHCONH—[pyridyl], CH₂-[3-phenoxy-(2-nitro-5-chlorophenyl)] ·2HCl | IR: 3400,3230,2925,2855, 1730,1640,1615,1605, 1580,1520,1503,1490, 1340<br>NMR: CD₃OD,TMS δ: 0.93–2.35(10H,m) 2.78(2H,d) 2.98–3.30(2H,m) 4.72–4.84(1H,m) 6.90–7.44(6H,m) 7.96–8.20(3H,m) 8.60(2H,d) |
| 50 | H₂NCH₂—[cyclohexyl]···CONHCHCONH—[cyclohexyl], CH₂-[3-(benzoyloxymethyl)phenyl] ·HCl | IR: 2935,2855,1700,1660, 1645,1530,1450,1350<br>NMR: CD₃OD,TMS δ: 0.80–2.30(20H,m) 2.70–3.08(4H,m) 4.44–4.58(1H,m) 5.42(2H,s) 6.56–7.68(8H,m) 8.00–8.08(1H,m) |
| 51 | H₂NCH₂—[cyclohexyl]···CONHCHCONH—CH(CO₂C₂H₅)—CH₂—[phenyl], CH₂-[3-phenoxyphenyl] (L) ·HCl | IR: 3280,2935,2855,1740, 1660,1640,1540,1255, 1210<br>NMR: CD₃OD,TMS δ: 0.84–2.24(13H,m) 2.76(2H,d) 2.80–3.20(4H,m) 4.04–4.19(2H,m) 4.57–4.72(2H,m) 5.03(2H,m) 6.69–7.45(14H,m) |
| 52 | H₂NCH₂—[cyclohexyl]···CONHCHCONH—[pyridyl], CH₂-[3-hydroxyphenyl] ·2HCl | IR: 3400–2800,1730,1640, 1610,1505,1480,1320, 1155<br>NMR: CD₃OD,TMS δ: 0.90–2.36(10H,m) 2.78(2H,d) 2.88–3.17(2H,m) 4.64–4.73(1H,m) 6.55–6.75(3H,m) 7.00–7.09(1H,m) 8.11(2H,d) 8.57(2H,d) |
| 53 | H₂NCH₂—[cyclohexyl]···CONHCHCONH—[4-benzoylphenyl], CH₂-[3-aminophenyl] ·2HCl | IR: 3400,2920,2580,1645, 1600,1520,1405,1310, 1250,700 |
| 54 | (H₂N)(HN=)C—NH(CH₂)₃CONHCHCONH—[phenyl]—CH=CH—CO₂CH₃·CH₃SO₃H, CH₂-[3-phenoxyphenyl] | IR: 3350,2950,1660,1595, 1535,1485,1410,1320, 1200,1055,835,780, 690 |

TABLE 1-continued

| No. | Compound | Physical Properties | |
|---|---|---|---|
| 55 | [structure: 4-amidinophenyl-CONHCH(CH2-3-phenoxyphenyl)CONH-phenyl · HI] | IR: 1680,1670,1635,1600, 1540,1485,1440,1400, 1245,1208 | NMR: CD$_3$OD,TMS δ: 3.10–3.30(2H,m) 4.80–4.90(1H,m) 6.76–8.00(18H,m) |
| 56 | [structure: 4-amidinophenyl-CONHCH(CH2-3-phenoxyphenyl)CONH(CH2)3CH3 · HI] | IR: 1650,1635,1490,1400, 1245,1210 | |
| 57 | [structure: 4-(H2NCH2)cyclohexyl-CONHCH(CH2-3-phenoxyphenyl)CO2C2H5 · HCl] | IR: 3360,2940,1745,1660, 1655,1645,1610,1588, 1530,1492,1250,1215 | NMR: CD$_3$OD,TMS δ: 0.90–2.28(10H,m) 1.20(3H,t) 2.78(2H,d) 2.82–3.20(2H,m) 4.10(2H,q) 4.52–4.68(1H,m) 6.76–7.38(9H,m) |
| 58 | [structure: 4-(H2NCH2)cyclohexyl-CONHCH(CH2-3-phenoxyphenyl)CO2H] | IR: 3375,2920,2860,1640, 1590,1580,1510,1500, 1485,1405,1390,1242, 1208 | |
| 59 | [structure: 4-(H2NCH2)cyclohexyl-CONHCH(CH2-3-phenoxyphenyl)CO2CH2-phenyl · HCl] | IR: 3300,2940,2860,1745, 1648,1600,1585,1490, 1250,1215 | NMR: CD$_3$OD,TMS δ: 0.88–2.24(10H,m) 2.77(2H,d) 2.85–3.20(2H,m) 4.57–4.69(1H,m) 5.08(2H,s) 6.76–7.36(14H,m) |
| 60 | [structure: 4-(H2NCH2)cyclohexyl-CONHCH(CH2-3-phenoxyphenyl)CO2CH2-pyridyl · 2HCl] | IR: 3425,3250,2940,2860, 1755,1660,1590,1540, 1490,1255,1215 | NMR: CD$_3$OD,TMS δ: 0.92–2.30(10H,m) 2.78(2H,d) 2.95–3.24(2H,m) 4.59–4.68(1H,m) 5.30(1H,d) 5.40(1H,d) 6.78–7.37(9H,m) 8.05–8.14(1H,m) 8.52–8.60(1H,m) 8.78–8.88(2H,m) |

TABLE 1-continued

| No. | Compound | Physical Properties | |
|---|---|---|---|
| 61 | 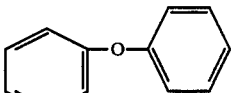 | IR: 3330,2940,1750,1735, 1648,1585,1525,1495, 1255,1210 | NMR: CD₃OD,TMS δ: 0.92–2.30(10H,m) 2.79(2H,d) 2.90–3.25(2H,m) 3.34(3H,s) 3.50–3.60(2H,m) 4.16–4.25(2H,m) 4.60–4.70(1H,m) 6.81–7.40(9H,m) |
| 62 | 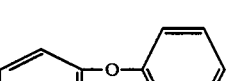 | IR: 3300,2940,2860,1750, 1655,1590,1490,1250, 1215 | |
| 63 |  | IR: 1745,1640,1560,1485, 1400,1245,1210 | |

The starting 3-substituted-DL-phenylalanines used in the synthesis of the compounds according to the present invention were newly prepared, other than commercially available 3-hydroxy-DL-phenylalanine. Of these phenylalanines, the 3-nitro substituted phenylalanines were prepared according to [J. Am. Chem. Soc., 81, 3103 (1959)] and the 3-trifluoromethyl substituted phenylalanines were prepared according to [J. Org. Chem., 25, 733 (1960).] The other 3-substituted phenylalanine were prepared according to [J. Am. Chem. Soc., 67, 308 (1945).] The typical examples of the above-mentioned methods are shown in the reaction route A below.

Reaction Route A

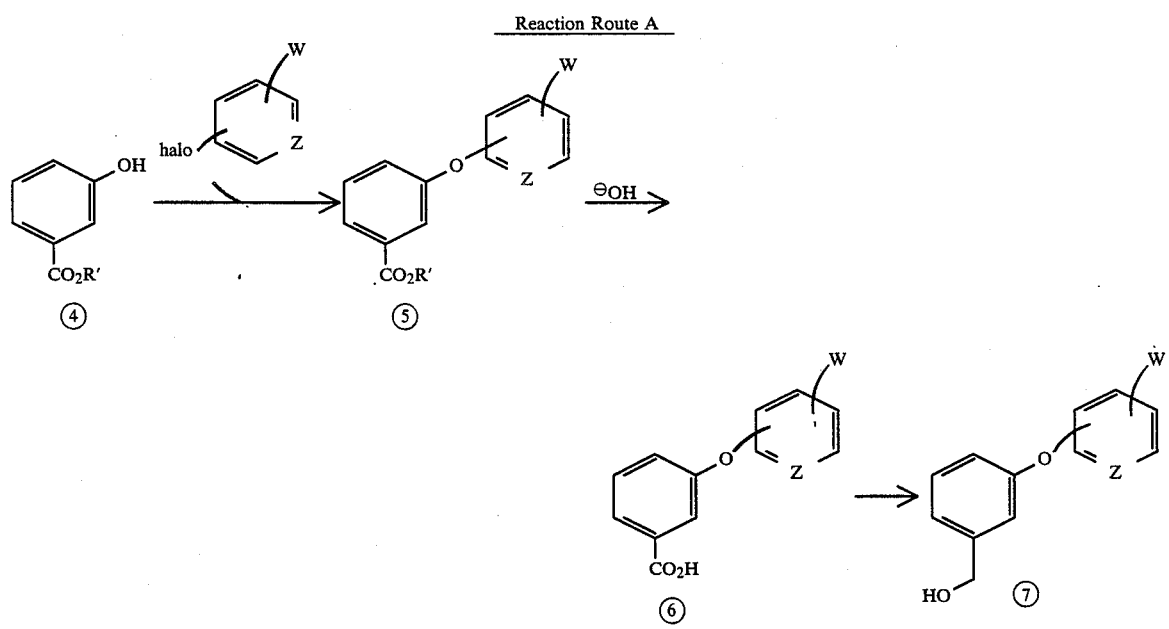

-continued
Reaction Route A

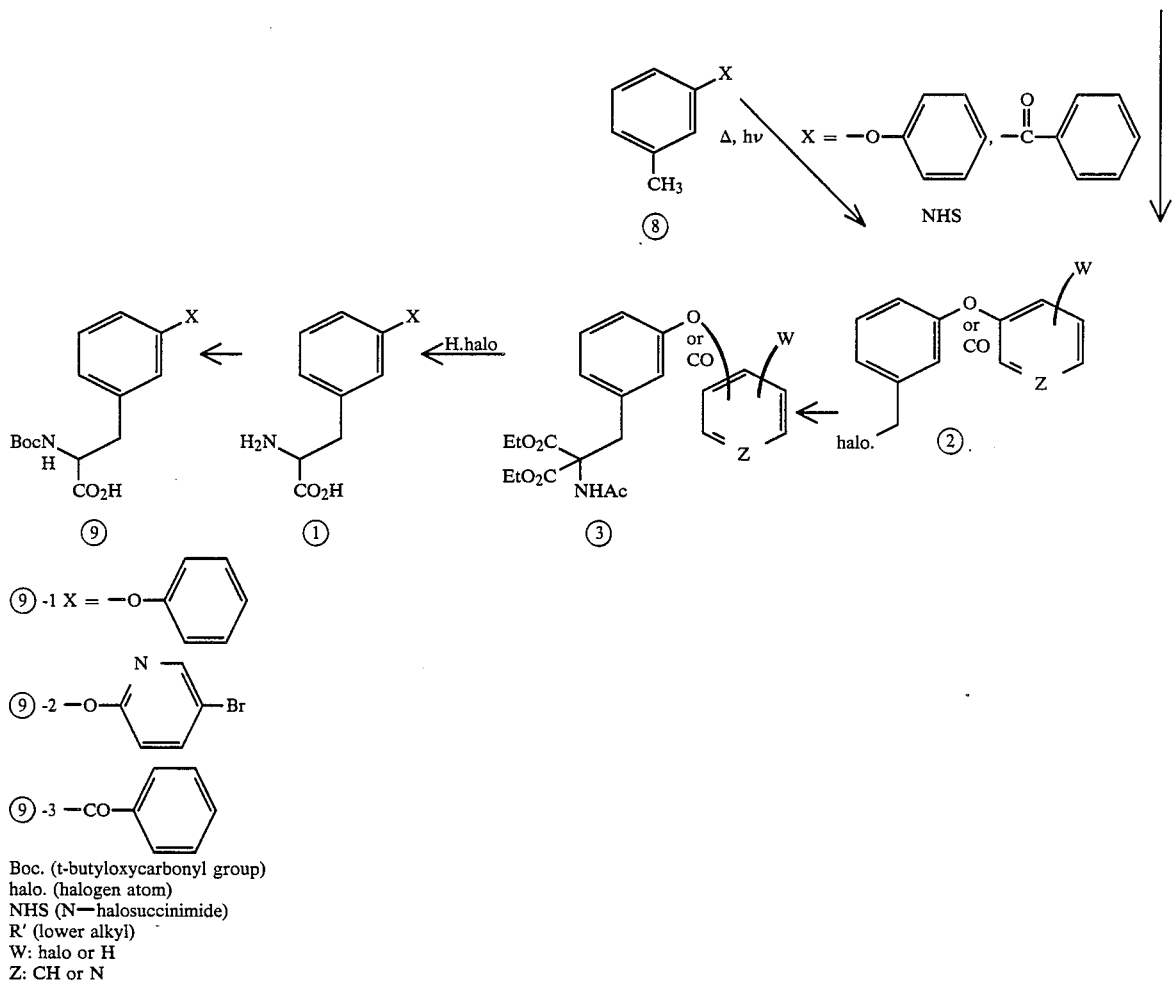

Boc. (t-butyloxycarbonyl group)
halo. (halogen atom)
NHS (N—halosuccinimide)
R' (lower alkyl)
W: halo or H
Z: CH or N Diarylethers are generally synthesized according to the so-called Ullman reaction by reacting phenol derivatives or their salts and aromatic halides in the absence or presence of copper or copper salt catalysts in the absence or presence of high-boiling point solvents such as toluene, N,N-dimethylformamide, and dimethylsulfoxide at an elevated temperature (e.g., 150° C. or more). When the aromatic halides are substitute with electron withdrawing groups such as nitro group and cyano group, the reaction can be carried out at a low temperature (e.g., room temperature to 50° C.). However, the preparation of the above-mentioned diarylethers having no substituents requires severe reaction conditions. When these severe conditions are applied to the preparation of 3-phenoxy-DL-phenylalanine, i.e., the reaction between 3-hydroxy-DL-phenylalanine and aromatic halides or 3-halo substituted-DL-phenylalanine and phenol derivatives, the starting materials and the products are likely to be decomposed and the isolation of the desired products is expected to be very difficult. Accordingly, according to the present invention, the 3-phenoxy-DL-phenylalanines are prepared according to the multi-step synthesis as shown in Routé A to eliminate the above-mentioned difficulties.

That is, when the compound ① is prepared, the commercially available compounds ④, ⑦, and ⑧ may be used as the starting material. The synthesis of the compound ① from the compound ⑦ is included the synthesis of the compound ① from the compound ④.

The synthesis of the compound ① from the compound ④ can be carried out as follows. That is, the compound ④ is dissolved at room temperature in an appropriate solvent such as N,N-dimethylformamide, dimethylsulfoxide, toluene, or hexamethylphosphoroustriamide and an appropriate base such as sodium hydride, potassium t-butoxide, sodium amide, or lithium diisopropylamide is added under ice-cooling in an amouht of, for example, 3 equivalents, more preferably 1.0 to 1.5 equivalents of the compound ④. Thereafter, the aromatic halide per se or dissolved in the solvent identical to the reaction solvent is added all at once or in several portions at room temperature in an amount of, for example, 1.0 to 1.5 equivalents of the compound ④, followed by allowing to react at a reaction temperature of 90° C.. to 150° C.. Optionally, copper or copper salts (e.g., copper chloride, copper bromide, or copper acetate) may be used as a catalyst in an amount of, for example, 0.01 to 0.02 equivalents relative to the compound ④. The reaction time is, for example, 1 to 48 hours, more preferably 2 to 12 hours. The post-treatment can be carried out as follows. That is, the reaction mixture is cooled to room temperature and the cooled mixture is poured into ice or ice-water. After neutralizing the pH, the mixture is extracted with an organic solvent, e.g., diethylether, ethyl acetate, dichloromethane, or chloroform, to remove the inorganic substances. The extract is washed with water, and after drying, the solvent is distilled off. The residue is then purified by recrystallization or distillation, optionally after the pretreatment by column chromatography. Thus, the desired aryloxy benzoates ⑤ can be obtained.

The reaction of the compound ⑥ from the compound ⑤ can be carried out as follows.

To the compound ⑤ per se or dissolved in an appropriate solvent such as methanol, ethanol, tetrahydrofuran, 1,4-dioxane, diethyl ether, or any mixture thereof at a concentration of, for example, 10% to 50% by weight, a 2N to 10N aqueous sodium hydroxide or potassium hydroxide is added at a temperature of, for example, 0° C.. to 100° C.., more preferably 20° C.. to 40° C.., in an amount of, for example, 1 to 10 equivalents, more preferably 1.5 to 2 equivalents to hydrolyze the ester ⑤. After completing the reaction, ice water and an appropriate organic solvent such as diethyl ether, benzene, or toluene are added to the reaction mixture to remove the unreacted compound ⑤. Thereafter, the pH of the resultant mixture is adjusted to 1 to 3, followed by extracting with an appropriate organic solvent such as diethylether, ethyl acetate, dichloromethane, or chloroform. The extract is washed with water and, after drying, the solvent is distilled off. The product is purified by recrystallization, optionally after the pretreatment by column chromatography. Thus, the desired carboxylic acid ⑥ is obtained.

The synthesis of benzyl alcohol derivatives from the compound ⑥ can be carried out as follows. That is, the compound ⑥ is dissolved in an anhydrous solvent such as tetrahydrofuran or diethyl ether, followed by dropwise addition of diboran under nitrogen or argon atmosphere at a temperature of, for example, 0° C.. to −20° C.. in an amount of 1 to 3 equivalents, more preferably 1.3 to 1.5 equivalents, relative to compound ⑥. After completing the reacting, diluted hydrochloric acid is added and the aqueous layer is separated. The organic layer is then washed with water, and after drying, the solvent is removed. The residue is purified, optionally after the pretreatment by column chromatography, by recrystallization or distillation to obtain the desired alcohol ⑦.

The synthesis of benzyl halides ② from the compound ⑦ is carried out as follows. That is, the compound ⑦, which is also commercially available, is dropwise added to thionyl chloride or thionyl bromide at a temperature of, for example, 0° C.. to 30° C.., more preferably 0° C.. to 10° C.. in an amount of 3 to 10 equivalents, preferably 4 to 6 equivalents, relative to the thionyl chloride or thionylbromide based on one equivalent of the compound ⑦. After completing the dropwise addition, the temperature of the mixture is returned to room temperature and the mixture is allowed to react for 6 to 72 hours, preferably 12 to 24 hours. After completing the reaction, the excess thionyl halide is removed in vacuo and the residue is purified by recrystallization or distillation to obtain benzyl halide ②.

The benzyl halides ② may also be obtained from the aryloxy toluene derivatives ⑧. That is, N-halosuccinimide is reacted with the aryloxy toluene derivative in an amount of 1 to 2 equivalents, preferably 1 to 1.2 equivalents, relative to the aryloxy toluene derivative in an appropriate solvent such as carbon tetrachloride, benzene, or 1,2-dichloroethane under reflux of the solvent for 30 minutes to 5 hours optionally in the presence of peroxides such as m-chloroperoxy acid or under light irradiation. After completing the reaction, the reaction mixture is cooled to room temperature. The reaction mixture is then washed with water, and after drying, the solvent is distilled off. The residue is purified by recrystallization or distillation to obtain the desired compound ②.

On the other hand, when 3-benzoyl-DL-phenylalanine is synthesized, the synthesis of phenylalanine by a Friedel-Crafts reaction is expected to be difficult because of the difference in the orientation, the compound ②-3 was prepared from the 3-benzoyl toluene ⑧-3.

The synthesis of the compound ③ from the benzyl halide derivative ② is carried out as follows. That is, to absolute ethanol in an amount of 100 to 300 ml, preferably 200 ml based on 0.1 mol of the compound ②, sodium is added in an amount equivalent to the compound ② to prepare a sodium ethoxide solution, followed by adding ethylacetaminomalonate in an amount equivalent to the compound ②. To this solution, the compound ② is added at room temperature to 100° C.., preferably under reflux of ethanol and the reaction mixture is allowed to react for 3 to 12 hours, preferably 6 to 8 hours. After completing the reaction, the solvent is distilled off in vacuo and the residue is extracted with an appropriate solvent such as chloroform, dichloromethane, or ethyl acetate. The organic layer is washed with water and, after drying, the solvent is distilled off. The residue is purified by recrystallization or by column chromatography in the case of the liquid product. Thus, the desired compound ③ can be obtained.

The synthesis of the 3-substituted phenylalanine ① from the compound ③ is carried out by reacting the compound ③ with concentrated or diluted hydrochloric acid or 48% hydrobromic acid in an amount of 500 ml to 1500 ml based on 1 mol of the compound 3 under reflux for 6 to 12 hours. After completing the reaction, the reaction mixture is cooled to room temperature, followed by adjusting the pH to 6 to 7 under ice-cooling with concentrated aqueous ammonia. The mixture is allowed to stand at room temperature or in a refrigerator for over night. The precipitated crystalline substance is collected by filtration, followed by washing with cooled water, acetone, diethyl ether. After drying, the desired compound ① can be obtained. The crystalline product thus obtained is substantially pure, as shown by various spectral data. Thus, no purification is necessary for the purpose of the present invention.

The 3-substituted-DL-phenylalanines obtained above are converted to t-butylcarbamate derivatives having a Boc group, which is a protective group of an amino group, used in the so-called peptide synthesis. This method is set forth in [Proc. Natl. Acad. Sci. USA, 69, 730 (1972), Bull. Chem. Soc. Jpn., 50, 718 (1977)]. The resultant compounds ⑨ are all in the form of while crystals and the structures thereof are confirmed by various spectral data. Furthermore, the 3-hydroxy-DL-phenylalanine ①-7 is converted to t-butylcarbamate derivative ⑨-6 according to the above-mentioned method after converting 3-benzyloxy-DL-phenylalanine ①-6 according to a method set forth in [Chem. Ber., 91, 542 (1958)].

The compounds of the present invention can be synthesized by various combinations of the so-called peptide synthesis methods and ester synthesis methods.

(1) Mixed acid anhydride method [Ann, Chem., 572, 190 (1951)]
(2) Acid halide method [Biochemistry., 4, 2219 (1965)]
(3) Phosphazo method [Chem. Ber., 93, 2387 (1960)]
(4) Carbodiimide method J. Am. Chem. Soc., 77, 1067 (1955), ibid., 84, 4457 (1962), Brochem. Biophy. Res. Comm., 52, No. 3 (1973), Chem. Ber., 103, 2034 (1970), Tetrahedron Lett., 46, 4475 (1978)]
(5) Active ester method using, for example, N-hydroxysuccinimide [J. Am. Chem. Soc., 85, 3039 (1963)].

It should be noted, however, that not all of the compounds can be synthesized according to the methods as mentioned here, and it is necessary to combine the above-mentioned methods appropriately for the respective compounds. Among these methods, typical examples of the reaction routes B and C are shown below.

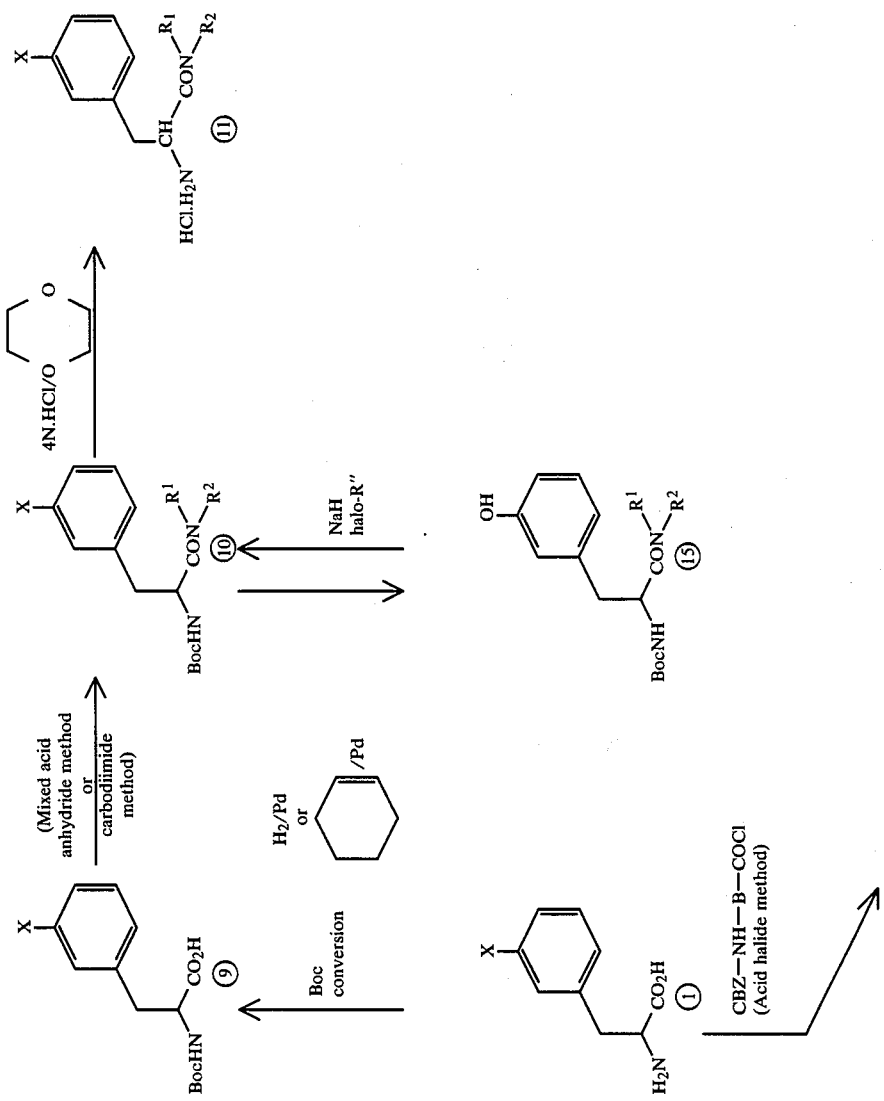

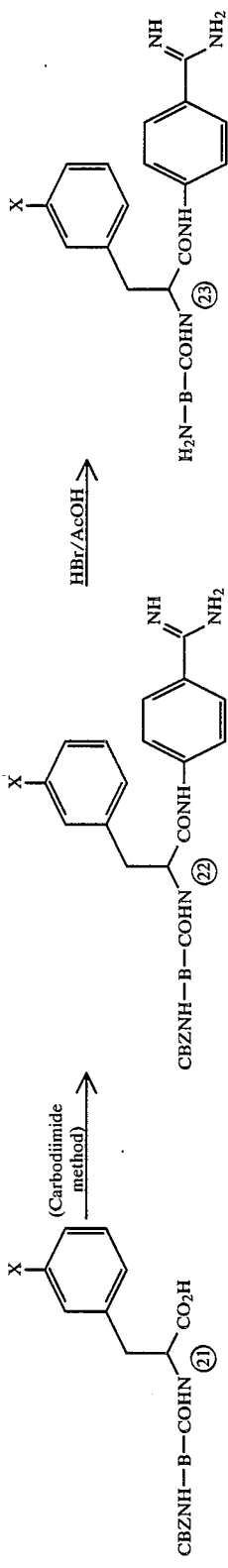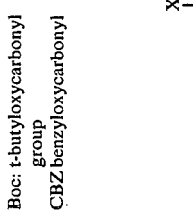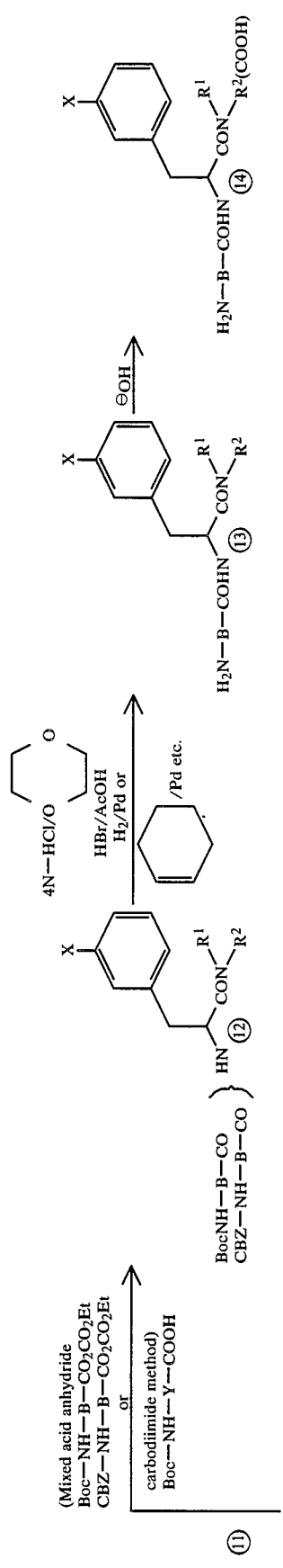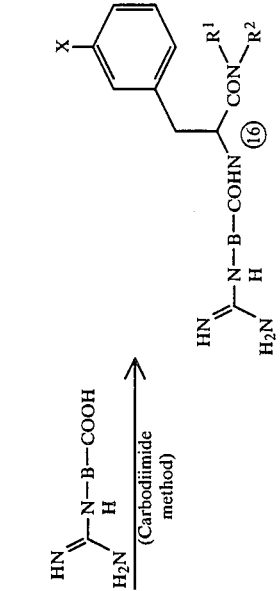

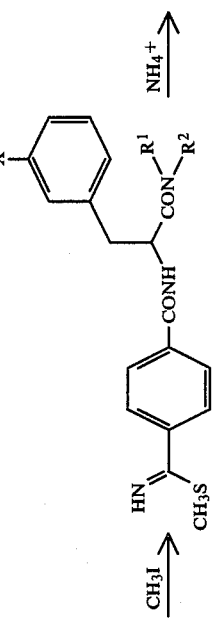

Reaction Route C

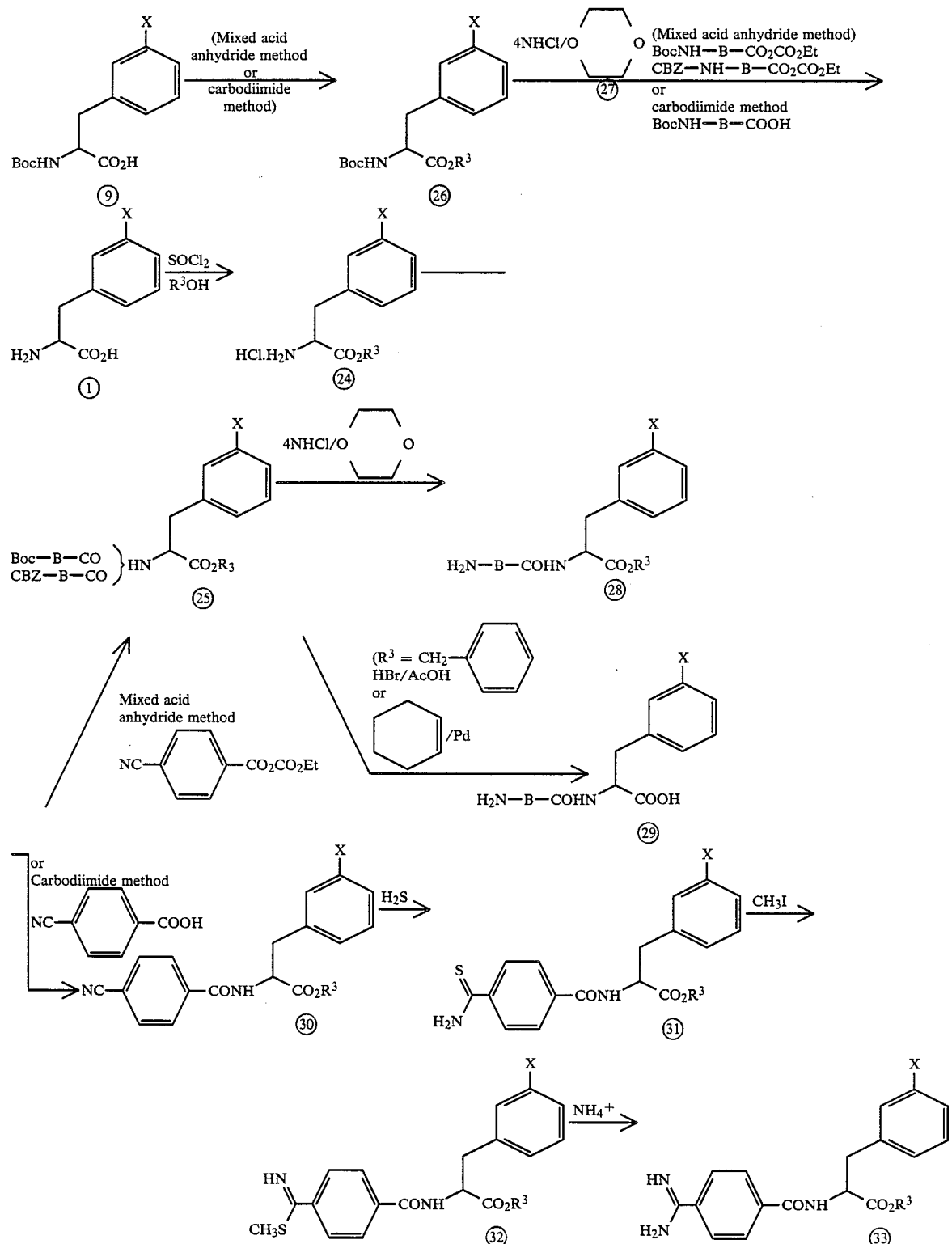

CBZ: benzyloxycarbonyl

For example, the synthesis from the compounds ⑨ to ⑩ and the syntheses from the hydrochloride ⑪ to the compounds ⑫, ⑯, and ⑰ in Route B and the syntheses from the hydrochloride ㉗ to the compound ㉕ and from the compound ㉔ to the compounds ㉕ and ㉚ can utilize the above-mentioned mixed acid anhydride method or carbodiimide method.

For example, the mixed acid anhydride method will now be explained.

For carrying out synthesis from the compounds ⑨ to ⑩, the compound ⑨ is dissolved in an appropriate dry solvent such as tetrahydrofuran diethyl ether, dioxane, or N,N-dimethylformamide, and an appropriate base such as triethylamine, or N-methylmorpholine is added in an amount of 1 to 5 equivalents, preferably 1 to 2 equivalents relative to the compound ①. To this reaction mixture is added 1 to 1.5 equivalents of ethyl chlorocarbonate as such or as a solution dissolved in the solvent used as the reaction solvent, at one time or in several divided portions. The temperature of the reaction mixture is maintained at −10° C.. to 10° C.., preferably −5° C.. to 5° C.. The reaction time is from 10 minutes to 3 hours, preferably from 15 minutes to 1 hour. After a conventional post-treatment, 0.5 to 2 equivalents of

are added and the reaction is carried out at −10° C.. to 30° C.., preferably −5° C.. to 20° C.., for 1 to 50 hours, preferably 2 to 20 hours.

After completing the reaction, the resultant solid substance is concentrated, directly or after filtration, concentrated in vacuo and the residue is extracted with an appropriate solvent such as diethyl ether, ethyl acetate, dichloromethane, or chloroform to remove the unreacted carboxylic acids and amines. After drying, the solvent is distilled off and the residue is purified by recrystallization or column chromatography to obtain the desired compound ⑩.

Furthermore, the above-mentioned carbodiimide method will now be explained below. The carbodiamide derivative is added, in an amount of 1 to 5 equivalents, preferably 1 to 2 equivalents, relative to the compound ⑨, to a solution containing of the compound ⑨,

in an amount of 1 to 5 equivalents, preferably 1 to 2 equivalents, relative to the compound ⑨, and an appropriate base such as triethylamine, pyridine, or N-methylmorpholine at a temperature of 0° C.. to room temperature and the reaction mixture is allowed to stand at a temperature of 0° C.. to room temperature for 1 to 24 hours. The solvent used in this reaction includes, for example dry dichloromethane, chloroform, acetonitrile, 1,4-dioxane, or pyridine. After completing the reaction, the precipitated substance, if any, is filtered off and the reaction mixture is extracted with an appropriate solvent such as diethyl ether, ethyl acetate, dichloromethane, or chloroform. The extract is purified in the manner according to the method in the above-mentioned mixed acid anhydride method. Thus, the desired compound ⑩ can be obtained.

The synthesis of the compound ⑪ from the compound ⑩ is carried out by adding a 4N-HCl/dioxane solution in an amount of 1 to 30 equivalents, 5 to 20 equivalents, relative to the compound ⑩. The reaction is carried out at 0° C.. to room temperature. After completing the reaction, a non-polar solvent such as hexane, pentane, heptane, or diethyl ether is added to recover the precipitated crystalline substance by filtration or by concentrating the solvent in vacuo to obtain the hydrochloride ⑪. Furthermore, the syntheses of the compounds ⑫, ⑯, and ⑰ from the compound ⑪, the compounds ㉓ from ㉗, and the compounds ㉕ and ㉚ from ㉔ can be carried out in the either manner as mentioned above.

In the reaction route B, the synthesis of the compound ⑮ from the compound ⑩ is carried out according to a method set forth in, for example, [Synthesis 685 (1976)] and [J. Chem. Soc., Perkin Trans 1, 490 (1977)]. The synthesis of the compound ⑩ from the compound ⑮ is carried out by dissolving the compound ⑮ an appropriate solvent such as N,N-dimethylformamide, dimethylsulfoxide, or toluene, followed by the addition of an appropriate base such as sodium hydride, potassium hydride, or potassium t-butoxide in an amount of 1 to 5 equivalents, preferably 1 to 2 equivalents, relative to the compound ⑮. To this mixture, halo-R″ as such or as dissolved in the solvent used as the reaction solvent and the resultant mixture is allowed to react at room temperature for 2 to 50 hours, preferably 4 to 6 hours. After completing the reaction, the desired compound ⑩ can be obtained by a post-treatment according to the ④ method mentioned in the synthesis of the compounds ⑤ from ④ above.

The synthesis of the compounds ㉖ from ⑨ in the Route C can be carried out in the manner used in the synthesis of the compounds ⑩ from ⑨, by substituting an alcohol component for the amine component.

Furthermore, the synthesis of the compounds ㉔ from ① in the Route C is carried out with reference to [Helv. Chim. Acta., 36, 1109 (1953)]. The synthesis of the compounds ⑳ from ⑰ in the Route B and the synthesis of the compounds ㉝ from ㉚ in the Route C are carried out with reference to a method set forth in [Synthetic Method 19, 378.] The removal of the benzyloxycarbonyl group (i.e., CBZ) is carried out in the manner used in the synthesis of the compounds ⑮ from ⑩ and also with reference to a method set forth in [J. Org. Chem., 17, 1564 (1952)].

EXAMPLES

The present invention will now be further illustrated by, but is by no means limited to, the following Examples. In the following, preparation of typical compounds is described by referring to specific examples.

EXAMPLE 1

Synthesis of
N-(t-butoxycarbonyl)-3-phenoxy-DL-phenylalanine (I)
(i.e., Compound ⑨-1 in the Route A)

(1) 3-Phenoxybenzyl alcohol (200 g) was dropwise added to thionyl chloride (520 g) under ice-cooling over one hour. The mixture was then stirred at room temperature for 24 hours, followed by distilling off excess thionyl chloride in vacuo. To be residue, toluene (500 ml) was added and, after distilling off the solvent, the resulting yellow oil was purified by distillation to obtain colorless oil (180.5 g) (b.p. 122°–124° C../1.5 mmHg), which was confirmed as 3-phenoxybenzyl chloride (II) by NMR spectral data.

(2) Ethylacetaminomalonate (140 g) was added to a sodium ethoxide solution prepared from absolute ethanol (1 liter) and sodium (15 g) and the mixture was allowed to react under reflux for 15 minutes. To the resultant reaction mixture, the compound (II) (141.5 g) obtained above was dropwise added at 80° C.. for 15 minutes. The mixture was then allowed to react under reflux of ethanol for 6 hours, and after cooling, the ethanol was distilled off in vacuo and the residue was extracted with dichloromethane. The organic layer was thoroughly washed with water and, after drying, the solvent was distilled off. The residue was recrystallized from diethyl ether-hexane to obtain ethyl 2-acetamide-2-carboxyethoxy-3-(3-phenoxy) phenyl propionate (III) (209.4 g) in the form of colorless prisms, which was confirmed by various spectral data.

NMR (CDCl$_3$, TMS) δ: 1.24 (6H, t), 1.96 (3H, s), 3.58 (2H, s), 4.06–4.30 (5H, m), 6.52–7.30 (9H, m).

(3) The compound (III) (205 g) obtained above and 48% hydrobromic acid (500 ml) were allowed to react under reflux for 7 hours. After cooling, concentrated aqueous ammonia was added, under ice-cooling, to adjust the pH to 6.5. While ice-cooling, the precipitated crystalline product was recovered by filtration. The product was washed with cold water, then, acetone, and diethyl ether, followed by drying. Thus, 3-phenoxy-DL-phenylalanine (IV) (138 g), which was confirmed by spectral data, was obtained in the form of a white powder.

(4) The compound (IV) (77.1 g) obtained above was suspended in a 1,4-dioxane-water (1/1) solution (450 ml) and triethylamine (143 ml) was then added thereto. After 15 minutes, di-t-butyldicarbonate (72 g) was added to the mixture, followed by stirring for one hour under ice-cooling and subsequently for 2 hours at room temperature. After completing the reaction, the reaction mixture was extracted with ethyl acetate (500 ml) and water (500 ml) to obtain an aqueous layer. To the aqueous layer, citric acid was added under ice-cooling to adjust the pH to weak acidity and the separated oily substance was extracted with ethyl acetate (500 ml). The organic layer was washed with water, and after drying, the solvent was distilled off in vacuo. The residue was crystallized from diethyl ether-hexane and, after recrystallization, N-(t-butoxycarbonyl)-3-phenoxy-DL-phenylalanine (I) (90.4 g), which confirmed by spectral data, was obtained in the form of a white prisms.

NMR (CDCl$_3$, TMS) δ: 1.30–1.48 (9H, m), 2.70–3.24 (2H, m), 4.30–4.70 (1H, broad), 4.90–5.04 (1H, broad) 6.80–7.35 (9H, m), 9.00–9.38 (1H, broad).

EXAMPLE 2

Synthesis of N-(t-butoxycarbonyl)-3-(5-bromo-2-pyridyloxy) DL-phenylalanine (I) (i.e., Compound ⑨-2 in the Route A)

(1) Ethyl 3-hydroxybenzoic acid (6.64 g) was dissolved in dimethylsulfoxide and oily sodium hydride (60% content) (1.60 g) was added thereto, followed by stirring at room temperature for 30 minutes. Then, 2,5-dibromopyridine (9.48 g) was added thereto and the mixture was allowed to react at 150° C.. for 4 hours. After cooling, the reaction mixture was poured to ice (100 g) and was extracted with diethyl ether. After washing four times with water, the extract was dried with anhydrous sodium sulfate and the solvent was distilled off. The residue was subjected to silica gel column chromatography. From the elute with hexanedichloromethane (1/1), ethyl 3-(5-bromo-2-pyridyloxy)benzoic acid (II) (9.40 g), which was confirmed by spectral data, was obtained in the form of a light yellow oil.

(2) The compound (II) (9.36 g) was dissolved in a mixed solvent (50 ml) of tetrahydrofuran/ethanol (1/1) and a 2N aqueous NaOH solution (21 ml) was then added at room temperature, followed by stirring for 2 hours. After completing the reaction, the reaction mixture was extracted with water (100 ml) and diethyl ether (50 ml). The aqueous layer thus obtained was weakly acidified by adding citric acid under ice-cooling to precipitate a crystalline product. The crystalline product was recovered by filtration and, after drying, 3-(5-bromo-2pyridyloxy)benzoic acid (III) (8.25 g), which was confirmed by NMR spectral data, was obtained in the form of white prisms (8.25 g).

(3) The carboxylic acid (III) obtained above (7.35 g) was dissolved, under nitrogen atmosphere, in anhydrous tetrahydrofuran (80 ml), followed by cooling in salt-ice bath. To this solution, a solution (16.75 ml) of 2M boran dimethylsulfide in diethyl ether was dropwise added over 15 minutes. After, stirring for 2 hours, ice water (50 ml) was added to the reaction mixture, followed by extracting with diethyl ether (100 ml). The extract was washed with water, and an aqueous sodium carbonate solution (twice), and after drying, the solvent was distilled off. The residue was subjected to silica gel column chromatography and, from the elute with hexane-dichloromethane (1:2), 3-(5-bromo-2-pyridyloxy)-benzyl alcohol (IV) (6.02 g), which was confirmed by NMR and IR analyses, as obtained in the form of colorless oil.

(4) The alcohol (IV) (6.00 g) obtained above was dropwise added to thionyl chloride (16 g) at room temperature for 5 minutes. After stirring for 24 hours, the excess thionyl chloride was distilled off in vacuo. Thereafter, toluene (30 ml) was added and was again distilled off. Diethyl ether was added to the residue and the precipitated insoluble matter was filtered off. The filtrate was concentrated to obtain 3-(5-bromo-2-pyridyloxy)benzyl chloride (V) (4.58 g), which was confirmed by an NMR analysis, was obtained in the state of an oil. This compound was used, without purifying, in the subsequent reaction.

(5) The benzyl chloride derivative (V) (4.55 g) was added to a reaction mixture prepared from absolute ethanol (150 ml), sodium (0.35 g), and ethylacetaminomalonate (3.30 g) at 50° C. at once and the mixture was allowed to react under reflux of ethanol for 6 hours. After cooling, the solvent was distilled off in vacuo and the residue was post-treated in the same manner as in Example 1-(2) to obtain ethyl 2-acetamide-2-carboethoxy-3-(5-bromo-2-pyridyoxy)phenyl pyopionate (VI) (7.00 g), which was confirmed by NMR and IR analyses, in the form of a yellow oil.

(6) To the compound (VI) (6.90 g) obtained above, concentrated hydrochloric acid (70 ml) was added and the mixture was allowed to react under reflux for 6 hours. After cooling, aqueous concentrated ammonia was added under ice-cooling to adjust the pH of the reaction mixture to 6.5. The precipitated crystalline product was recovered by filtration, and after washing with ice water, the crystalline product was further washed with acetone and diethyl ether, followed by drying. Thus, 3-(5-bromo-2-pyridyloxy)-DL-phenylalanine (VII) (4.44 g), which was confirmed by spectral data, was obtained in the form of a white powder.

(7) The compound (VII) (4.20 g) obtained above was suspended in water (40 ml) and 1,4-dioxane (10 ml) and triethylamine (6.0 ml) was further added. To this solution, a solution of 2-t-butoxycarbonyloxyimino-2-phenylacetnitrile (VIII) (3.06 g) in 1,4-dioxane (20 ml) was added at once at room temperature. The mixture was allowed to react at room temperature for 3 hours. Water (40 ml) and ethyl acetate (30 ml) were added to remove the unreacted compound (VIII). The aqueous layer was made weak acidic with citric acid. The separated oily product was extracted with ethyl acetate, followed by washing with water and drying. After distilling off the solvent in vacuo, the desired compound (I) (5.04 g), which was confirmed by NMR and IR analyses, was obtained in the amorphous state.

EXAMPLE 3

Synthesis of
N-(t-butoxycarbonyl)-3-benzoyl-DL-phenylalanine
(i.e., Compound ⑨-3 in the Route A)

3-Methylbenzophenone (10.0 g), N-bromosucciniimide (7.30 g), and m-chloroperoxybenzoic acid (0.03 g) were charged into anhydrous benzene (150 ml) and the mixture was allowed to react under reflux of benzene for one hour by photoirradiation. After cooling, ice water was added and the organic layer was washed. After drying, the organic layer was concentrated in vacuo to obtain 3-benzoylbenzylbromide (II), which was confirmed by an NMR analysis, in the form of a pale yellow oil. The compound (II) was reacted in the same manner as in Examples 1 and 2. Thus, the desired amorphous compound (I) (5.20 g) was finally obtained.

EXAMPLE 4

Synthesis of
N-(trans-4-aminomethylcyclohexylcarbonyl)-3-phenoxy-DL-phenylalanine 4-acetylanilide
hydrochloride (Compound No. 2)

N-(t-butoxycarbonyl)-3-phenoxy-DL-phenylalanine (I) (7.42 g) obtained in Example 1 was dissolved in dry tetrahydrofuran (80 ml), triethylamine (3 ml) was added to the resultant solution and ethyl chlorocarbonate (2.40 g) was added to the mixture under ice-cooling, followed by stirring for 30 minutes. To this solution was added 4-acetylaniline (2.70 g) and the mixture was stirred at room temperature for 10 hours. To the reaction mixture was added ice-water (300 ml) and the precipitated crystalline substance was collected by filtration, thoroughly washed and dried to obtain 7.07 g of N-(t-butoxycarbonyl)-3-phenoxy-DL-phenylalanine 4-acetylanilide (II), which was confirmed by IR and NMR analyses.

To the above compound (II) (2.29 g) was added under ice-cooling 4N-hydrogen chloride/1,4-dioxane solution (30 ml). The ice-cooling was then stopped and the compound then stirred at room temperature for 30 minutes. To this solution was added diethyl ether (300 ml) and the precipitated crystalline substance was collected by filtration, washed with diethyl ether and dried under a reduced pressure to quantitatively obtain 3-phenoxy-DL-phenylalanine 4-acetylanilide hydrochloride (III).

On the other hand, trans-4-(t-butoxycarbonyl)aminomethylcyclohexylcarbonxylic acid (1.62 g) was dissolved in dry tetrahydrofuran (50 ml) and dry N,N-dimethylformamide (20 ml), triethylamine (0.96 ml) was added to the resultant solution and a solution of ethyl chlorocarbonate (0.76 g) in tetrahydrofuran (2 ml) was added to the mixture under ice-cooling, followed by stirring for 30 minutes. To this solution was added the hydrochloride (III) previously obtained and triethylamine (2 ml) was added to the mixture, followed by stirring at room temperature for 3 hours. Ice-water (200 ml) was added to the reaction mixture and the precipitated crystalline substance was collected by filtration, thoroughly washed with water and dried to obtain 2.62 g of N-[trans-4-(t-butyloxycarbonyl)aminomethylcyclohexylcarbonyl]-3-phenoxy-DL-phenylalanine 4-acetylanilide (IV) in the form of a white powder. The compound (IV) was confirmed by an NMR analysis.

To the above compound (IV) (2.60 g) was added under ice-cooling 4N-hydrogen chloride/1,4-dioxane solution (25 ml) and the mixture was stirred at room temperature for 30 minutes. Diethyl ether (100 ml) was added to this solution and the precipitated crystalline substance was collected by filtration, followed by washing with diethyl ether. After drying in vacuo, N-(trans-4-aminomethylcyclohexylcarbonyl)-3-phenoxy-DL-phenylalanine 4-acetylanilide hydrochloride (V) (1.90 g) was obtained in the form of a white powder.

The trans-4-(t-butoxycarbonyl)aminomethylcyclohexylcarboxylic acid used above was prepared as follows.

Trans-4-aminomethylcyclohexylcarboxylic acid (15.7 g) was suspended in 300 ml of a mixture of water/1,4-dioxane (1/1). Triethylamine (45 ml) was then added and, after the mixture became uniform, di-t-butyl dicarbonate (24.0 g) was added under ice-cooling at once. The ice bath was removed, and after the mixture was stirred at room temperature for 3 hours, water (150 ml) and ethyl acetate (150 ml) was added to effect the extraction. The resultant aqueous layer was recovered and was weak acidified under ice-cooling with citric acid. The separated oily substance was extracted with ethyl acetate (300 ml) and the organic layer was washed with water and saturated aqueous sodium chloride solution. After drying over anhydrous sodium sulfate, the solvent was distilled off in vacuo. The crystalline residue was recrystallized from diethyl ether-hexane to obtain trans-4-(t-butoxycarbonyl)aminomethylcyclohexylcarboxylic acid (24.1 g).

EXAMPLE 5

Synthesis of
N-(trans-4-aminomethylcyclohexylcarbonyl)-3-phenoxy-DL-phenylalanine 2-ethoxycarbonylanilide
hydrochloride (Compound No. 4)

N-(t-butoxycarbonyl)-3-phenoxy-DL-phenylalanine (0.72 g) and triethylamine (0.25 g) were dissolved in dry tetrahydrofuran (15 ml) and ethyl chlorocarbonate (0.22 g) was added under ice-cooling, followed by stirring for 20 minutes. Ethyl anthranylate (0.33 g) was then added, followed by stirring at room temperature for 12 hours. Thus, N-(t-butoxycarbonyl)-3-phenoxy-DL-phenylalanine 2-ethoxycarbonylanilide (I) (0.80 g), which was confirmed by NMR and IR analyses, was obtained in the form of a white powder according to a conventional post-treatment.

To the compound (I) (0.50 g), a 4N-hydrogen chloride/1,4-dioxane solution (1.5 ml) was added, followed by stirring at room temperature for 30 minutes. To this solution, diethyl ether (10 ml) was added and the precipitated solid was recovered by filtration to obtain 3-phenoxy-DL-phenylalanine 2-ethoxycarbonylanilide hydrochloride (II) (0.40 g).

On the other hand, trans-4-(t-butoxycarbonyl)aminomethylcyclohexylcarboxylic acid (0.233 g) and triethylamine (0.22 g) were dissolved in dry tetrahydrofuran (15 ml) and ethyl chlorocarbonate (0.10 g) was then added, followed by stirring for 20 minutes. To this solution, the compound (II) was added and the mixture was stirred at room temperature for 12 hours. Thus, according to a conventional post-treatment, N-trans-4-(t-butoxycarbonyl)aminomethylcyclohexylcarbonyl-3-phenoxy-DL-phenylalanine 2-ethoxycarbonylanilide (III) (0.38 g), which was confirmed by an NMR analysis, was obtained in the form of a pale yellow powder.

The compound (III) (0.38 g) was dissolved in a 4N-hydrogen chloride/1,4-dioxane solution (0.9 ml) and the mixture was stirred at room temperature for 30 minutes. Diethyl ether (10 ml) was added and the precipitated crystalline substance was recovered by filtration. Thus, N-(trans-4-aminomethylcyclohexylcarbonyl)-3-phenoxy-DL-phenylalanine 2-ethoxycarbonylanilide hydrochloride (0.30 g), which was confirmed by spectral data, was obtained in the form of a white powder.

EXAMPLE 6

Synthesis of
N-(trans-4-aminomethylcyclohexylcarbonyl)-3-phenoxy-DL-phenylalanine-4-amidinoanilide dihydrochloride (Compound No. 5)

To 3-phenoxy-DL-phenylalanine (2.0 g) and potassium carbonate (1.4 g), water (50 ml), and 1,4-dioxane (25 ml) were added. After the mixture became uniform, N-[trans-(4-benzyloxycarbonyl)aminomethylcyclohexylcarbonyl]chloride (2.0 g) was added, followed by allowing to stand for one night.

After distilling off the 1,4-dioxane, diluted hydrochloric acid was added and the precipitated crystalline substance was recovered by filtration. The crystalline substance was thoroughly washed with water, followed by drying. Thus, N-[trans-(4-benzyloxycarbonyl)aminomethylcyclohexylcarbony-]3-phenoxy-DL-phenylalanine (I) (1.5 g), which was confirmed by an NMR analysis, in the form of a pale yellow crystal was obtained.

The compound (I) (1.0 g) was dissolved in anhydrous pyridine (5 ml) and, after the mixture became uniform, N,N-dicyclohexyl carbodiimide (0.4 g) was added under ice-cooling, followed by stirring for 30 minutes. Thereafter, 4-amidinoaniline dihydrochloride (0.4 g) was gradually added and the mixture was allowed to stand in a refrigerator for one night. The precipitated substance was filtered off and the pyridine was distilled off. The resultant reaction mixture was made weak acidic with citric acid and was then washed with water. The resultant crystalline substance was recovered by filtration, followed by recrystallizing from methanol and water. Thus, N-[trans-(4-benzylocycarbonyl)aminomethylcyclohexylcarbonyl]-3-phenoxy-DL-phenylalanine 4-amidinoanilide (II) (0.6 g), which was confirmed by an NMR analysis, was obtained in the form of a pale orange crystal.

To the compound (II) (0.46 g) obtained above, 30%-hydrogen bromide/CH$_3$COOH (1 ml) was added and the mixture was stirred at room temperature. After 15 minutes, diethyl ether was added and was then removed by decantation, followed by post-treating with saturated sodium bicarbonate/chloroform. The chloroform was distilled off to obtain white crystalline substance (0.2 g). Then, 4N-hydrogen chloride/1,4-dioxane was added and the mixture was stirred for 20 minutes. Thereafter, hexane was added and then removed by decantation. Thus, N-(trans-4-aminomethylcyclohexylcarbonyl)-3-phenoxy-DL-phenylalanine 4-amidinoanilide dihydrochloride (0.2 g), which was confirmed by NMR analysis, was obtained in the form of a pale yellow powder.

EXAMPLE 7

Synthesis of
N-(trans-4-aminomethylcyclohexylcarbonyl)-3-phenoxy-DL-phenylalanine 4-pyridylamide dihydrochloride (Compound No. 8)

N-(t-butoxycarbonyl)-3-phenoxy-DL-phenylalanine (2.14 g) was dissolved in dry tetrahydrofuran (50 ml) and triethylamine (0.90 ml) was added under ice-cooling. After stirring for 10 minutes, a solution of ethyl chlorocarbonate (0.66 g) in dry tetrahydrofuran (2 ml) was further added, followed by allowing to react for 30 minutes. Thereafter, 4-aminopyridine (0.56 g) was added and the mixture was stirred at 0° C. for one hour and at room temperature for 4 hours. After the solid was filtered, the filtrate was concentrated in vacuo, followed by extracting with ethyl acetate. The extract was washed 4 times with water and saturated aqueous sodium chloride solution, followed by drying over anhydrous sodium sulfate. After distilling off the solvent in vacuo, diethyl ether was added to the resultant oily residue to crystallize the residue. Thus, N-(t-butoxycarbonyl)-3-phenoxy-DL-phenylalanine 4-pyridylamide (I) (1.98 g), which was confirmed by an NMR analysis, was obtained in the form of a white powder.

The compound (I) (1.73 g) was dissolved in dry 1,4-dioxane (10 ml) and a 4N-hydrogen chloride/1,4-dioxane solution (30 ml) was added, followed by stirring at room temperature for one hour. The precipitated white crystalline substance was recovered by filtration, was washed with diethyl ether, and was dried in vacuo. Thus, 3-phenoxy-DL-phenylalanine 4-pyridylamide dihydrochloride (II) (1.62 g), which was confirmed by an NMR analysis, was obtained in the form of a white powder.

On the other hand, trans-4-(t-butoxycarbonyl)aminomethylcyclohexylcarboxylic acid (1.03 g) was dissolved in dry tetrahydrofuran (40 ml) and dry N,N-dimethylformamide (15 ml) and triethylamine (0.60 ml) was then added. To this mixture, a solution (1.5 ml) of ethyl chlorocarbonate (0.44 g) in dry tetrahydrofuran was added, followed by stirring for 20 minutes. To this solution, the dihydrochloride (II) (1.62 g) was added and triethylamine (1.20 ml) was further added, followed by stirring for 30 minutes under ice-cooling and for 3 hours at room temperature. After completing the reaction, the solid was filtered off and the solvent was distilled off in vacuo. Thereafter, ice water (100 ml) was added and the precipitated crystalline substance was recovered by filtration, followed by thoroughly washing with water and drying. Thus, N-[trans-4-(t-butoxycarbonyl)aminomethylcyclohexylcarbonyl]-3-phenoxy-DL-phenylalanine 4-pyridylamide (III) (1.70 g) which was confirmed by spectral data, was obtained in the form of a white powder.

The compound (III) (1.60 g) was dissolved in dry 1,4-dioxane (5 ml) and a 4N-hydrogen chloride/1,4-dioxane solution (30 ml) was added, followed by stirring at room temperature. After one hour, the precipitated crystalline substance was recovered by filtration, followed by washing with diethylether, and after drying in vacuo, the desired N-(trans-4-aminomethylcyclohexylcarbonyl)-3-phenoxy-DL-phenylalanine 4-pyridylamide dihydrochloride (1.57 g), which was confirmed by NMR spectrum analysis, was obtained in the form of a hygroscopic white powder.

EXAMPLE 8

Synthesis of N-(trans-4-aminomethylcylohexylcarbonyl)-3-phenoxy-DL-phenylalanine 4-(2-chloro)pyridylamide dihydrochloride (Compound No. 9)

N-(t-butoxycarbonyl)-3-phenoxy-DL-phenylalanine (4.40 g) was dissolved in dry tetrahydrofuran (100 ml) and triethylamine (1.80 ml) was added under ice-cooling, followed by stirring for 15 minutes. To this solution was added ethyl chlorocarbonate (1.44 g) and the mixture was stirred for 30 minutes. After adding 4-amino-2-chloropyridine (1.54 g), the reaction was carried out at room temperature for 10 hours. Thereafter, the solid was filtered off and the filtrate was concentrated under a reduced pressure. The residue was extracted with ethyl acetate. The extract was purified with a column chromatography (hexane/ethyl acetate=3/1) to obtain N-(t-butoxycarbonyl)-3-phenoxy-DL-phenylalanine 4-(2-chloro)pyridylamide (I) (0.60 g), which was confirmed by the following NMR analysis, in the form of a white powder.

NMR (CDCl$_3$) δ: 1.42 (9H, s), 2.96–3.20 (2H, m), 4.37–4.53 (1H, m), 5.10–5.21 (1H, m) 6.80–7.50 (11H, m), 8.21 (2H, d), 8.60–8.80 (2H, brs)

Following the procedure of Examples 4, 5, and 7 the final compound N-(trans-4-aminomethylcyclohexylcarbonyl)-3-phenoxy-DL-phenylalanine 4-(2-chloro)-pyridylamide dihydrochloride (II) (0.70 g) was obtained in the form of hygroscopic white powder from the compound (I).

EXAMPLE 9

Synthesis of N-(trans-4-aminomethylcyclohexylcarbonyl)-3-phenoxy-DL-phenylalanine 2-nicotinylamide dihydrobromide (Compound No. 10)

Trans-(4-benzyloxycarbonyl)aminomethylcyclohexylcarboxylic acid (3.0 g) was dissolved in chloroform (20 ml) and thionyl chloride (1.39 g) was added thereto at room temperature. After allowing to stand for 5 hours, the reaction mixture was concentrated in vacuo. The resultant residue was dissolved in dry 1,4-dioxane (20 ml) and triethylamine (3.03 g) and further 3-phenoxy-DL-phenylalanine hydrochloride (3.05 g) were added. The mixture was stirred at room temperature for 10 hours. N-[trans-(4-benzyloxycarbonyl)aminomethylcyclohexylcarbonyl]-3-phenoxy-DL-phenylalanine (I) (3.75 g), which was confirmed by an NMR analysis, was obtained by a conventional post-treatment in the form of white powder.

The compound (I) (0.30 g) and triethylamine (0.1 g) were dissolved in dry tetrahydrofuran (15 ml) and ethyl chlorocarbonate (0.06 g) was added thereto under ice-cooling followed by stirring for 20 minutes. Thereafter, 2-aminonicotinic acid (0.08 g) was further added and the mixture was stirred at room temperature for 12 hours. Thus, N-[trans-(4-benzyloxycarbonyl)aminomethylcyclohexylcarbonyl]-3-phenoxy-DL-phenylalanine 2-nicotinylamide (II) (0.30 g), which was confirmed by NMR analysis, was obtained in the form of a pale yellow powder by a conventional post-treatment.

The compound (II) (0.30 g) was treated with a 30% hydrogen bromide/acetic acid solution (1.5 ml) to obtain the desired final product, N-(trans-4-aminomethylcyclohexylcarbonyl)-3-phenoxy-DL-phenylalanine 2-nicotinylamide dihydrobromide (0.25 g) in the form of a white powder.

EXAMPLE 10

Synthesis of N-(trans-4-aminomethylcyclohexylcarbonyl)-3-phenoxy-DL-phenylalanine 4-pyrimidylamide dihydrochloride (Compound No. 12)

N-(t-butoxycarbonyl)-3-phenoxyphenylalanine (1 g) was dissolved in dry tetrahydrofuran (30 ml) and triethylamine (2 ml) was added thereto. Thereafter, ethyl chlorocarbonate (0.3 g) was added under ice-cooling, followed by stirring for 30 minutes. To this solution, 4-aminopyrimidine (0.24 g) was added, followed by stirring at room temperature for 10 hours. After distilling off the solvent, the residue was extracted with ethyl acetate, followed by washing with water. After drying, the solvent was distilled off to obtain N-(t-butoxycarbonyl)-3-phenoxy-DL-phenylalanine 4-pyrimidylamide (I) (1.5 g), which was confirmed as a substantially pure product by an NMR analysis, in the form of a white powder.

Following the procedure of Examples 4, 5, and 7, the final compound, N-(trans-4-aminomethylcyclohexylcarbonyl)-3-phenoxy-DL-phenylalanine 4-pyrimidylamide dihydrochloride (II) (0.70 g) was obtained in the form of a white powder from the compound (I).

EXAMPLE 11

Synthesis of N-(trans-4-amnomethylcyclohexylcarboonyl)-3-phenoxy-DL-phenylalanine 3-methoxypropylamide hydrochloride (Compound No. 14)

N-(t-butoxycarbonyl)-3-phenoxy-DL-phenylalanine (1.07 g) was dissolved in dry tetrahydrofuran (30 ml) and, under ice-cooling, triethylamine (0.45 ml) was added. After stirring for 10 minutes, a solution of ethyl chlorocarbonate (0.33 g) in dry tetrahydrofuran (2 ml) was added all at once, followed by stirring for 30 minutes. Thereafter, 3-methoxypropylamine (0.29 g) was added at once, followed by stirring under ice-cooling for 30 minutes and at room temperature for 2 hours. After filtering off the solid material, the reaction mixture was concentrated in vacuo and the residue was extracted with ethyl acetate. The organic layer was washed with, in this order, 10% citric acid, water, aqueous sodium bicarbonate, and saturated aqueous sodium chloride. After drying over anhydrous sodium sulfate, the solvent was distilled off in vacuo. The precipitated crystalline substance was recovered with diisopropyl ether by filtration, followed by drying. Thus, N-(t-butoxycarbonyl)-3-phenoxy-DL-phenylalanine 3-methoxypropylamide (I) (1.02 g), which was confirmed by an NMR analysis, was obtained in the form of a white powder.

Following the procedure of Examples 4, 5, and 7, the final compound N-(trans-4-aminomethylcyclohexylcarbonyl)-3-phenoxy-DL-phenylalanine 3-methoxypropylamide hydrochloride (II) (0.35 g) was obtained in the form of hygroscopic white powder from the compound (I).

EXAMPLE 12

Synthesis of N-(trans-4-aminomethylcyclohexylcarbonyl)-3-phenoxy-DL-phenylalanine amide hydrochloride (Compound No. 21)

N-(t-butoxycarbonyl)-3-phenoxy-DL-phenylalanine (0.59 g) was suspended in benzene (10 ml) and phosphorus pentachloride (0.51 g) was added under ice-cooling, followed by stirring for 20 minutes. After stirring at room temperature for 5 minutes, the mixture was concentrated in vacuo. The residue was dissolved in dry 1,4-dioxane (10 ml) and a saturated aqueous ammonia/1,4-dioxane solution (10 ml) was then added thereto, followed by stirring at room temperature for 2 hours. After the reaction mixture was concentrated in vacuo, the residue was added to a solution prepared by dissolving trans-4-(t-butoxycarbonylaminomethylcyclohexylcarboxylic acid (0.43 g) and triethylamine (0.20 g) in dry tetrahydrofuran (10 ml) and, then, by adding ethyl chlorocarbonate (0.18 g) under ice-cooling, followed by stirring. The mixture was stirred for 12 hours. N-[trans-4-(t-butoxycarbonyl)aminomethylcyclohexylcarbonyl]-3-phenoxy-DL-phenylalanine amide (I) (0.50 g), which was confirmed by an NMR analysis, was obtained in the form of powder by a conventional post-treatment.

The compound (I) (0.25 g) was dissolved in a 4N-hydrogen chloride/1,4-dioxane solution (0.76 ml) and the solution was stirred at room temperature for 30 minutes. Diethyl ether (10 ml) was added and the precipitated substance was recovered by filtration. After drying, N-(trans-4-aminomethylcyclohexylcarbonyl)-3-phenoxy-DL-phenylalanine amide hydrochloride (0.18 g), which was confirmed by an IR analysis, was obtained in the form of a white powder.

EXAMPLE 13

Synthesis of N-(trans-4-aminomethylcyclohexylcarbonyl)-3-benzyloxy-DL-phenylalanine 3-pyridylamide dihydrochloride (Compound No. 22)

N-(t-butoxycarbonyl)-3-benzyloxy-DL-phenylalanine (3.71 g) was dissolved in dry tetrahydrofuran (100 ml), and under ice cooling, triethylamine (1.5 ml) was added thereto. After stirring for 15 minutes, a solution of ethyl chlorocarbonate (1.10 g) in dry tetrahydrofuran (1 ml) was added, followed by stirring for 30 minutes. To this solution was added 3-aminopyridine (0.94 g) and the reaction was carried out at room temperature for 7 hours. The solid was filtered off and the filtrate was concentrated under reduced pressure. The residue was extracted with ethyl acetate. The organic layer was washed with water for three times and with saturated aqueous sodium chloride solution, followed by drying over anhydrous sodium sulfate. After the solvent was distilled off, the oily residue was obtained. To the oily residue, diethyl ether was added to form crystalline substance. Thus, N-(t-butoxycarbonyl)-3-benzyloxy-DL-phenylalanine 3-pyridylamide (I) (3.03 g), which was confirmed by various spectral data, was obtained in the form of a white powder.

Following the procedure of Examples 4, 5, and 7, the final compound N-(trans-4-aminomethylcyclohexylcarbonyl)-3-benzyloxy-DL-phenylalanine 3-pyridylamide dihydrochloride (II) (2.70 g) was obtained in the form of hygroscopic white powder from the compound (I).

EXAMPLE 14

Synthesis of N-(trans-4-aminomethylcyclohexylcarbonyl)-3-(5-bromo-2-pyridyloxy)-DL-phenylalanine 3-methoxypropylamide hydrochloride (Compound No. 25)

N-(t-butoxycarbonyl)-3-(5-bromo-2-pyridyloxy)-DL-phenylalanine (0.44 g) obtained in Example 2 was dissolved in dry tetrahydrofuran (10 ml) and triethylamine (0.15 ml) was added under ice-cooling. After stirring for 10 minutes, a solution of ethyl chlorocarbonate (0.11 g) in dry tetrahydrofuran (1 ml) was added all at once, followed by stirring for 30 minutes. Then, 3-methoxypropylamine (0.09 g) was added at once, followed by stirring at room temperature for 2 hours. The solid material was filtered off, followed by concentrating in vacuo. The residue was extracted with ethyl acetate and the organic layer was washed with water, 10% aqueous citric acid, water, and saturated aqueous sodium chloride solution, followed by drying over anhydrous sodium sulfate. After distilling off the solvent in vacuo, N-(t-butoxycarbonyl)-3-(5-bromo-2-pyridyloxy)-DL-phenylalanine 3-methoxypropylamide (I) (0.46 g), which was confirmed by an NMR analysis, was obtained in the form of yellow oil.

Following the procedure of Examples 4, 5, and 7, the final compound N-(trans-4-aminomethylcyclohexylcarbonyl)-3-(5-bromo-2-pyridyloxy)-DL-phenylalanine 3-methoxypropylamide hydrochloride (II) (0.27 g) was obtained in the form of hygroscopic white powder from the compound (I).

EXAMPLE 15

Synthesis of N-(trans-4-aminomethylcyclohexylcarbonyl)-3-trifluoromethyl-DL-phenylalanine morpholinoamide hydrochloride (Compound No. 29)

N-(t-butoxycarbonyl)-3-trifluoromethyl-DL-phenylalanine (0.30 g) was dissolved in dry tetrahydrofuran (10 ml) and, under ice-cooling, triethylamine (0.13 ml) was further added. After stirring for 10 minutes, a solution of ethyl chlorocarbonate (0.10 g) in dry tetrahydrofuran (0.5 ml), followed by stirring for 30 minutes. Thereafter, morpholine (0.10 g) was added at once and the mixture was stirred at room temperature for 2 hours. After filtering off the solid substances, the resultant reaction mixture was concentrated in vacuo. The residue was extracted with ethyl acetate and the organic layer was washed with water, a 10% aqueous citric acid, water, a 5% aqueous sodium bicarbonate, and a saturated aqueous sodium chloride, followed by drying over anhydrous sodium sulfate. After concentrating in vacuo, N-(t-butoxycarbonyl)-3-trifluoromethyl-DL-phenylalanine morpholinoamide (I) (0.28 g), which was confirmed by an NMR analysis, was obtained in the form of a colorless oil.

Following the procedure of Examples 4, 5, and 7, the final compound N-(trans-4-aminomethylcyclohexylcarbonyl)-3-trifluoromethyl-DL-phenylalanine morpholinoamide hydrochloride (II) (0.17 g) was obtained in the form of hygroscopic white powder from the compound (I).

EXAMPLE 16

Synthesis of
N-(trans-4-guanidinomethylcyclohexylcarbonyl)-3-phenoxy-DL-phenylalanine 4-acetylanilide methane sulfonate (Compound No. 30)

3-Phenoxy-DL-phenylalanine 4-acetylanilide hydrochloride (I) was prepared in the same manner as in Example 4. The compound (I) (0.41 g), trans-4-guanidinomethylcyclohexylcarboxylic acid hydrochloride (0.24 g) prepared according to a method set forth in Chem. Pharm. Bull., 33, 647 (1985), and N,N-dicyclohexylcarbodiimide (0.23 g) were dissolved in dry pyridine (5 ml), followed by stirring for 20 hours. After the insoluble matter was filtered off, the filtrate was concentrated in vacuo and a saturated aqueous sodium bicarbonate solution was added to the residue, followed by stirring for 2 hours. The precipitated crystalline substance was recovered by filtration, and after washing thoroughly with water, the resultant crystalline substance was dried. The substance, after confirming by NMR and IR analyses, was dissolved in methanol (5 ml) and methanesulfonic acid (0.04 g) was added, followed by stirring at room temperature for 20 minutes. Diethyl ether (20 ml) was added to the resultant solution and the precipitated crystalline substance was recovered by filtration. After washing with diethyl ether and drying, N-(trans-4-guanidinomethylcyclohexylcarbonyl)-3-phenoxy-DL-phenylalanine 4-acetylanilide methane sulfonate (0.22 g) was obtained in the form of a white powder.

EXAMPLE 17

Synthesis of
N-(4-guanidinobenzoyl)-3-phenoxy-DL-phenylalanine 4-ethoxycarbonyl piperidinoamide methane sulfonate (Compound No. 34) and
N-(4-guanidinobenzoyl)-3-phenoxy-DL-phenylalanine 4-hydroxycarbonyl piperidinoamide methane sulfonate (Compound Nos. 34 and 35)

N-(t-butoxycarbonyl)-3-phenoxy-DL-phenylalanine (2 g) and 4-ethoxycarbonylpiperidine (0.58 g) were dissolved in dry dichloromethane (30 ml) and the condensation agent, 1-ethyl-3-(3-dimethylaminopropyl)carbodiimide hydrochloride (1.1 g) was then added, followed by stirring at room temperature for 12 hours. After the reaction, the reaction mixture was washed with water, alkaline water, and acidic water, followed by drying over anhydrous sodium sulfate. After distilling off the solvent, the resultant pale yellow solid was recrystallized from dichloromethane-diethyl ether to obtain N-(t-butoxycarbonyl)-3-phenoxy-DL-phenylalanine 4-ethoxycarbonylpiperidinoamide (I) (2.4 g), which was confirmed by IR and NMR analyses.

The compound (I) (2 g) was added to a 4N-hydrogen chloride/1,4-dioxane solution (5 ml) and, under ice-cooling, the mixture was stirred for 30 minutes. After the reaction, diethyl ether was added and the precipitated solid substance was washed several times with diethyl ether. Thus, 3-phenoxy-DL-phenylalanine 4-ethoxycarbonylpiperidinoamide hydrochloride (2) (1.6 g), which was confirmed by IR and NMR analyses, was obtained in the form of pale yellow solid.

The compound (II) (0.7 g) and 4-guanidinobenzoic acid (0.36 g) were dissolved in dry pyridine (20 ml) and the above-mentioned condensation agent was then added, followed by allowing to stand at room temperature for 24 hours. After the reaction, the solvent was distilled off and the residue was washed several times with a saturated aqueous sodium bicarbonate solution. Thus, N-(4-guanidinobenzoyl)-3-phenoxy-DL-phenylalanine 4-ethoxycarbonylpiperidinoamide carbonate (III) (0.65 g) was obtained in the form of yellowish brown solid. The compound (III) (0.65 g) was dissolved in methanol (5 ml) and methanesulfonic acid (0.11 g) was added to the resultant solution. The mixture was allowed to stand for 30 minutes and diethyl ether was added thereto. The precipitated solid was washed several times with diethyl ether to obtain N-(4-guanidinobenzoyl)-3-phenoxy-DL-phenylalanine 4-ethoxycarbonylpiperidinoamide methane sulfonate (IV) (0.67 g) (i.e., Compound No. 34) in the form of a pale brown solid.

The compound (III) (0.65 g) and sodium carbonate (0.3 g) were added to a water-1,4-dioxane mixed solution (30 ml), followed by refluxing upon heating for 5 hours. After allowing to stand at room temperature for one night, the precipitated solid was recovered by filtration and was dissolved in a dichloromethane-ethanol mixed solution (10 ml). To this solution, methanesulfonic acid (0.3 g) was added. After allowing to stand for 30 minutes, diethyl ether was added. The precipitated solid was washed several times with diethyl ether to obtain N-(4-guanidinobenzoyl)-3-phenoxy-DL-phenylalanine 4-hydroxycarbonylpiperidinoamide methane sulfonate (0.55 g) (Compound 35) was obtained in the form of a pale brown solid.

EXAMPLE 18

Synthesis of
N-(4-guanidinobenzoyl)-3-phenoxy-DL-phenylalanine 4-ethoxycarbonylmethylanilide (Compound No. 43)
and
N-(4-guanidinobenzoyl)-3-phenoxy-DL-phenylalanine 4-hydroxycarbonylmethylanilide hydrochloride (Compound No. 36)

N-(t-butoxycarbonyl)-3-phenoxy-DL-phenylalanine (3 g) was dissolved in dry tetrahydrofuran and triethylamine (8 ml) was then added, followed by adding ethyl chlorocarbonate (1 g) under ice-cooling. After the mixture was stirred for 30 minutes, 4-ethoxycarbonylmethylaniline hydrochloride (1.6 g) was added, followed by stirring at room temperature for 10 hours. After the solvent was distilled off, the residue was extracted with ethyl acetate, followed by washing with water and drying. Thus, N-(t-butyloxycarbonyl)-3-phenoxy-DL-phenylalanine 4-ethoxycarbonylmethylanilide (I) (2.3 g) was obtained in the form of a white powder.

To the compound (I) (1.0 g), a 4N-HCl/1,4-dioxane solution (10 ml) was added under ice-cooling, followed by stirring at room temperature for 30 minutes. Hexane (30 ml) was added to the resultant solution and the precipitated crystalline substance was recovered by filtration, followed by washing with diethyl ether. After distilling off the solvent in vacuo, 3-phenoxy-DL-phenylalanine 4-ethoxycarbonylmethylanilide hydrochloride (II) (0.6 g) was obtained in the form of a white powder.

On the other hand, 4-guanidinobenzoic acid (0.15 g) was dissolved in pyridine and, under ice-cooling, N,N-dicyclohexylcarbodiimide (0.16 g) was then added, followed by stirring for 30 minutes. To this mixture, the compound (II) (0.3 g) was added, followed by allowing to stand in a refrigerator for one night. The precipitate was filtered off, and the pyridine was distilled off. Thus, N-(4-guanidinobenzoyl)-3-phenoxy-DL-phenylalanine 4-ethoxycarbonylmethylanilide (III) (0.3 g) (i.e., Compound No. 43), which was confirmed by an NMR analysis, was obtained in the form of brown powder.

The compound (III) (0.2 g) was dissolved in tetrahydrofuran (10 ml)/methanol (4 ml) and sodium hydroxide (0.02 g)/water (2 ml) were added, followed by stirring at 40° C. for one hour. After distilling off the solvent, the resultant mixture was neutralized with citric acid and the precipitated crystalline substance was recovered by filtration. Thus, N-(4-guanidinobenzoyl)-3-phenoxy-DL-phenylalanine 4-hydroxycarbonylmethylanilide (IV) (0.2 g) was obtained in the form of a pale brown powder. To this powder, a 4N-HCl/1,4-dioxane solution (2 ml) was added under ice-cooling, followed by stirring at room temperature for 20 minutes. Diethyl ether was added to the resultant solution and the precipitated crystalline substance was recovered by filtration. The recovered crystalline substance was recrystallized from methanol/diethyl ether to obtain N-(4-guanidinobenzoyl)-3-phenoxy-DL-phenylalanine 4-hydroxycarbonylmethylanilide hydrochloride (0.12 g) in the form of a white powder.

EXAMPLE 19

Synthesis of
N-(4-aminomethylbenzoyl)-3-phenoxy-DL-phenylalanine 4-(2-methoxycarbonylvinyl)anilide hydrochloride (Compound No. 42) and
N-(4-aminomethylbenzoyl)-3-phenoxy-DL-phenylalanine 4-(2-hydroxycarbonylvinyl)anilide hydrochloride (Compound No. 37)

After 4-aminomethylbenzoic acid (10 g) and t-butyloxycarbonyloxyimino-2-phenylacetonitrile (19 g) was dissolved in water-1,4-dioxane mixed solution (200 ml), triethylamine (14 g) was added thereto, followed by stirring at room temperature for 12 hours. After the reaction, the solvent was distilled off and water (100 ml) was added, followed by washing with ethyl acetate. The mixture was acidified with citric acid, and was extracted with ethyl acetate, followed by drying over anhydrous sodium sulfate. After distilled off the solvent, the residue was recrystallized from chloroform to obtain 4-(t-butyloxycarbonyl)aminomethylbenzoic acid (I) (14 g) in the white solid.

The compound (I) (0.28 g) and 3-phenoxy-DL-phenylalanine 4-(2-methoxycarbonylvinyl)anilide hydrochloride (0.16 g) were dissolved in a dry dichloromethanetriethylamine mixed solvent and the condensation agent, 1-ethyl-3-(3-dimethylaminopropyl)carbodiimide hydrochloride (0.17 g) was then added, followed by stirring at room temperature for 12 hours. After the reaction, the reaction mixture was washed with water, alkaline water, and acidic water, followed by drying over anhydrous sodium sulfate. After distilling off the solvent, the residue was recrystallized from a dichloromethane-diethyl ether mixed solvent. Thus, N-[4-(t-butoxycarbonyl)aminomethylbenzoyl]-3-phenoxy-DL-phenylalanine 4-(2-methoxycarbonylvinyl)anilide (II) (0.3 g), which was confirmed by IR and NMR analyses, was obtained in the form of a white solid.

To the compound (III) a 4N-HCl/1,4-dioxane solution (5 ml) was added, followed by stirring for 30 minutes under ice-cooling. After the reaction, diethyl ether was added to cause the precipitation, followed by washing several times with diethyl ether. Thus, N-(4-aminomethylbenzoyl)-3-phenoxy-DL-phenylalanine 4-(2-methoxycarbonylvinyl)anilide hydrochloride (IV) (0.2 g) (i.e., Compound No. 42) was obtained in the form of a pale yellow solid.

The compound (IV) (0.13 g) and sodium carbonate (0.05 g) were added to a water-1,4-dioxane mixed solvent (30 ml), followed by refluxing upon heating for 4 hours. After the reaction, the reaction mixture was allowed to stand for one night and the precipitated solid was recovered by filtration. The recovered solid was dissolved in a saturated hydrogen chloride/methanol solution. The resultant solution was allowed to stand for 10 minutes, followed by distilling off the solvent. The residue was recrystallized from a methanol-diethyl ether mixed solvent to obtain N-(4-aminomethylbenzoyl)-3-phenoxy-DL-phenylalanine 4-(2-hydroxycarbonylvinyl)anilide hydrochloride (0.11 g) in the form of a white solid.

EXAMPLE 20

Synthesis of
N-(trans-4-aminomethylcyclohexylcarbonyl)-3-benzoyl-DL-phenylalanine 2-(4-ethoxycarbonylmethyl)thiazolylamide hydrochloride (Compound No. 39)

N-(t-butoxycarbonyl)-3-benzoyl-DL-phenylalanine (0.37 g) was dissolved in dry tetrahydrofuran (8 ml) and triethylamine was then added under ice-cooling. After stirring for 10 minutes, a solution of ethyl chlorocarbonate (0.11 g) in dry tetrahydrofuran (1 ml) was added at once, followed by stirring for 30 minutes. Thereafter, ethyl(2-amino-4-thiazole)acetate (0.19 g) was added and the mixture was then stirred at room temperature for 5 hours. The solid was filtered off and, after concentrating in vacuo, the residue was extracted with ethyl acetate. The organic layer was washed with water (thrice), 10% aqueous citric acid, 5% aqueous sodium bicarbonate, and saturated aqueous sodium chloride solution, followed by drying over anhydrous sodium sulfate. After concentrating in vacuo, the residue was subjected to silica-gel column chromatography and N-(t-butoxycarbonyl)-3-benzoyl-DL-phenylalanine 2-(4-ethoxycarbonylmethyl)thiazolylamide (I) (0.37 g), which was confirmed by an NMR analysis, was obtained in the form of pale yellow oil from the elute by hexane/ethyl acetate (3/1).

To the compound (I) (0.37 g), a 4N-HCl/1,4-dioxane solution (4 ml) was added and the mixture was stirred at room temperature for one hour. Hexane (30 ml) was added and the precipitated oily substance was obtained by decantation from the upper layer. The product was thoroughly washed with diethyl ether, and after drying in vacuo, hygroscopic white powder (0.33 g) was obtained.

On the other hand, to a mixed acid anhydride prepared from 4-(t-butoxycarbonyl)aminomethylcyclohexyl carboxylic acid (0.20 g), triethylamine (0.12 ml), and ethyl chlorocarbonate (0.09 g), the white powder (0.33 g) obtained above was added and N,N-dimethylformamide (5 ml) and triethylamine (0.12 ml) were further added, followed by stirring at room temperature for 2 hours. Ice water (50 ml) was then added and the separated oily substance was extracted with ethyl acetate. The organic layer was washed with water (thrice), 10% aqueous citric acid, water, 5% aqueous sodium bicarbonate, and saturated aqueous sodium chloride solution, followed by drying over anhydrous sodium sulfate. After concentrating in vacuo, the residue was subjected to silica-gel column chromatography. Thus, N-[trans-4-(t-butoxycarbonyl)aminomethylcyclohexylcarbonyl]-3-benzoyl-DL-phenylalanine 2-(4-ethoxycarbonylmethyl)thiazolylamide (II) (0.15 g), which was confirmed by an NMR analysis, was obtained in the form of a colorless oil from the elute by hexane/ethyl acetate (2/1).

To the compound (II) (0.13 g), a 4N-HCl/1,4-dioxane solution (2 ml) was added, followed by stirring at room temperature for one hour. The solvent was concentrated in vacuo and diethyl ether was added to the residue to pulverize the resultant substance. The powder was recovered by filtration and was then dried in vacuo. Thus, N-(trans-4-aminomethylcyclohexylcarbonyl)-3-benzoyl-DL-phenylalanine 2-(4-ethoxycarbonylmethyl)thiazolylamide hydrochloride (0.11 g) was obtained in the form of a hygroscopic white powder.

EXAMPLE 21

Synthesis of
N-(trans-4-aminomethylcyclohexylcarbonl)-3-nitro-DL-phenylalanine 4-benzoylanilide hydrochloride
(Compound No. 44)

N-(t-butoxycarbonyl)-3-nitro-DL-phenylalanine (1.90 g) and triethylamine (0.8 ml) were dissolved in dry tetrahydrofuran (30 ml), and ethyl chlorocarbonate (0.66 g) was added under ice-cooling to the resultant solution, followed by stirring for 20 minutes. 4-benzoylaniline (1.2 g) was added to the solution and the mixture was further stirred at room temperature for 12 hours.

The solid material was filtered off, followed by concentrating the filtrate in vacuo. The residue was extracted with ethyl acetate, followed by washing with a 10% aqueous citric acid solution and water. After drying over anhydrous sodium sulfate, the solvent was distilled off in vacuo. The residue was crystallized from diethyl ether to obtain N-(t-butoxycarbonyl)-3-nitro-DL-phenylalanine 4-benzoylanilide (I), which was confirmed by IR and NMR analyses, was obtained in the form of pale yellow crystal.

Following the procedure of Examples 4, 5, and 7, the final compound N-(trans-4-aminomethylcyclohexylcarbonyl)-3-nitro-DL-phenylalanine 4-benzoylanilide hydrochloride (II) (0.50 g) was obtained in the form of a light yellow powder from the compound (I).

EXAMPLE 22

Synthesis of
N-(4-aminomethylbenzoyl)-3-phenoxy-DL-phenylalanine 2-ethoxycarbonylethylamide hydrochloride
(Compound No. 45)

N-(t-butoxycarbonyl)-3-phenoxy-DL-phenylalanine (1.78 g) was dissolved in a mixed solvent of dry tetrahydrofuran (30 ml) and dry N,N-dimethylformamide (10 ml) and, under ice-cooling, triethylamine (0.75 ml) was added. After stirring for 10 minutes, a solution of ethyl chlorocarbonate (0.55 g) in dry tetrahydrofuran (2 ml) was added, followed by stirring for 30 minutes. To this solution, β-alanine ethyl ester hydrochloride (0.77 g), and further, triethylamine (0.75 ml) was added, followed by stirring at room temperature for 2 hours. After the solid material was filtered off, the resultant mixture was concentrated in vacuo and the residue was extracted with ethyl acetate. After the organic layer was washed with water (thrice), 10% aqueous citric acid, water, and saturated aqueous sodium chloride solution, the organic layer was dried over anhydrous sodium sulfate, followed by concentrating in vacuo. The crystallized residue was recovered with diisopropyl ether by filtration. Thus, N-(t-butoxycarbonyl)-3-phenoxy-DL-phenylalanine 2-ethoxycarbonylethylamide (I) (1.74 g), which was confirmed by an NMR analysis, was obtained in the form of a white powder.

To the compound (I) (0.47 g), a 4N-hydrogen chloride/1,4-dioxane solution (4 ml) was added, followed by stirring at room temperature for 1 hour. Diethyl ether was then added and the precipitated crystalline substance was recovered by filtration, followed by drying in vacuo. Thus, a hygroscopic white powder (0.35 g) was obtained.

On the other hand, 4-(t-butoxycarbonyl)aminomethyl benzoic acid (0.25 g) was dissolved in a mixed solvent of dry tetrahydrofuran (8 ml) and dry N,N-dimethylformamide (4 ml), and triethylamine (0.15 ml) was then added under ice-cooling. After stirring for 10 minutes, a solution of ethyl chlorocarbonate (0.11 g) in dry tetrahydrofuran (1 ml) was added, followed by stirring for 20 minutes. To this solution, the white powder (0.35 g) obtained above was added, followed by stirring at room temperature for 3 hours. The solid was filtered off, and after concentrating in vacuo, the mixture was extracted with ethyl acetate. The organic layer was washed with water (thrice), 10% aqueous citric acid, water, and saturated sodium chloride solution, followed by drying over anhydrous sodium sulfate and concentrating in vacuo. The residue was crystallized from diethyl ether. Thus, N-[4-(t-butoxycarbonyl)aminomethylbenzoyl]-3-phenoxy-DL-phenylalanine 2-ethoxycarbonylethylamide (II) (0.34 g), which was confirmed by an NMR analysis, was obtained in the form of a white powder.

To the compound (II) (0.30 g), a 4N-hydrogen chloride/1,4-dioxane solution (3 ml) was added, followed by stirring at room temperature for 2 hours. The separated oily substance was recovered by decantating the upper layer, followed by washing with diethyl ether. After drying in vacuo, the oily substance was crystallized from diethyl ether to obtain N-(4-aminomethylbenzoyl)-3-phenoxy-DL-phenylalanine 2-ethoxycarbonylethylamide hydrochloride (0.28 g) in the form of a white powder.

EXAMPLE 23

Synthesis of
N-(4-aminomethylbenzoyl)-3-benzoyl-DL-phenylalanine benzylamide hydrochloride (Compound No. 47)

N-(t-butoxycarbonyl)-3-benzoyl-DL-phenylalanine (0.24 g) was dissolved in dry tetrahydrofuran (5 ml) and, under ice-cooling, triethylamine (0.10 ml) was added, followed by stirring for 10 minutes. Thereafter, a solution of ethyl chlorocarbonate (0.07 g) in dry tetrahydrofuran (0.5 ml) was added, followed by stirring for 30 minutes. Benzylamine (0.05 g) was further added and the mixture was stirred at room temperature for 2 hours. The solid was filtered off and, after concentrating in vacuo, the residue was extracted with ethyl acetate. The organic layer was washed with, in this order, water, 10% aqueous citric acid, water, and saturated sodium chloride solution, followed by drying over anhydrous sodium sulfate and concentrating in vacuo. The residue was crystallized from diethyl ether to obtain N-(t-butoxycarbonyl)-3-benzoyl-DL-phenylalanine benzylamide (I) (0.12 g) in the form of a white powder, which was confirmed by an NMR spectrum analysis.

Following the procedure of Example 22, the final compound N-(4-aminomethylbenzoyl)-3-benzoyl-DL-phenylalanine benzylamide hydrochloride (II) (0.10 g) was obtained in the form of a white powder from the compound (I).

EXAMPLE 24

Synthesis of N-(trans-4-aminomethylcyclohexylcarbonyl)-3-(5-nitro-2-pyridyloxy)-DL-phenylalanine 4-acetylanilide hydrochloride (Compound No. 48)

A mixture of N-(t-butoxycarbonyl)-3-benzyloxy-DL-phenylalanine 4-acetylanilide (I) (4.88 g) which was prepared in the same manner as in Example 13, palladium black (0.60 g), cyclohexene (15 ml) and ethanol (100 ml) was subjected to the reaction under reflux of ethanol for 1 hour. After cooling, the solid was filtered off and the filtrate was concentrated to obtain N-(t-butoxycarbonyl)-4-hydroxy-DL-phenylalanine 4-acetylanilide (II) (3.90 g), which was confirmed by an NMR spectrum analysis.

The compound (II) was used in a subsequent reaction without purification. To a solution of the compound (II), in dry dimethylsulfoxide (100 ml) was added oily sodium hydride (60% content) (0.41 g), followed by stirring at room temperature for 30 minutes. Then, 2-chloro-5-nitropyridine (1.59 g) was added and stirred at room temperature or 10 hours. After a conventional post-treatment, N-(t-butoxycarbonyl)-3-(5-nitro-2-pyridyloxy)-DL-phenylalanine 4-acetylanilide (III) (4.50 g), which was confirmed by an NMR spectrum analysis, was obtained in the form of a yellow powder. The above compound (III) (4.50 g) was treated with 4N-hydrogen chloride/1,4-dioxane solution (70 ml) to obtain 3-(5-nitro-2-pyridyloxy)-DL-phenylalanine 4-acetylanilide hydrochloride (IV) (3.95 g) in the form of white powder, which was confirmed by an NMR spectrum analysis.

Following the procedure of Examples 4, 5, and 7, the final compound N-(trans-4-aminomethylcyclohexylcarbonyl)-3-(5-nitro-2-pyridyloxy)-DL-phenylalanine 4-acetylanilide hydrochloride (V) (3. 45 g) was obtained in the form of a light yellow powder from the compound (IV).

EXAMPLE 25

Synthesis of N-(trans-4-aminomethylcyclohexylcarbonyl)-3-(3-chloro-6-nitrophenoxy)-DL-phenylalanine 4-pyridylamide dihydrochloride (Compound No. 49)

To a solution of N-(t-butoxycarbonyl)-3-hydroxy-DL-phenylalanine 4-pyridylamide (5.35 g) which was prepared in the same manner as in Example 24, in dimethyl sulfoxide (100 ml) was added oily sodium hydride (60% content) (0.62 g), followed by stirring at room temperature for 30 minutes. Thereafter, 2,4-dichloronitrobenzene (2.88 g) was added and stirred at room temperature for 10 hours. After a conventional post-treatment for example of Example 24, N-(t-butoxycarbonyl)-3-(3-chloro-6-nitrophenoxy)-DL-phenylalanine 4-pyridylamide (I) (6.66 g) was obtained in the form of a yellow powder.

Following the procedure of Examples 4, 5, and 7, the final compound N-(trans-4-aminomethylcyclohexylcarbonyl)-3-(3-chloro-6-nitrophenoxy)-DL-phenylalanine 4-pyridylamide dihydrochloride (II) (6.06 g) was obtained in the form of a light yellow powder from the compound (I).

EXAMPLE 26

Synthesis of N-(trans-4-aminomethylcyclohexylcarbonyl)-3-phenacyloxy-DL-phenylalanine cyclohexylamide hydrochloride (Compound No. 50)

A mixture of N-(t-butoxycarbonyl)-3-benzyloxy-DL-phenylalanine cyclohexylamide, which was prepared in the same manner as in Example 13, (I) (0.68 g), palladium black (0.10 g), cyclohexene (4 ml), and ethanol (20 ml) was allowed to react under reflux of ethanol for one hour, while stirring. After cooling, the solid was filtered off and the filtrate was concentrated under reduced pressure to obtain N-(t-butoxycarbonyl)-3-hydroxy-DL-phenylalanine cyclohexylamide (II) (0.54 g). The compound (II) (0.54 g) was dissolved, without purfication, in N,N-dimethylformamide (10 ml), followed by adding oily sodium hydride (60% content) (0.06 g) thereto. The mixture was stirred at room temperature for 30 minutes. To this solution was added a solution of phenacyl bromide (0.30 g) in N,N-dimethylformamide (5 ml). The reaction was carried out at room temperature for 4 hours, followed by adding ice-water thereto. The resultant oily product was extracted with ethyl acetate. After a conventional post-treatment, N-(t-butoxycarbonyl)-3-phenacyloxy-DL-phenylalanine cyclohexylamide (III) (0.61 g) was obtained.

Following the procedure of Examples 4, 5, and 7, the final compound N-(trans-4-aminomethylcyclohexylcarbonyl)-3-phenacyloxy-DL-phenylalanine cyclohexylamide hydrochloride (0.50 g) (IV) was obtained in the form of a white powder from the compound (III).

EXAMPLE 27

Synthesis of N-(trans-4-aminomethylcyclohexylcarbonyl)-3-hydroxy-DL-phenylalanine 4-pyridylamide dihydrochloride (Compound No. 52)

N-(t-butoxycarbonyl)-3-benzyloxy-DL-phenylalanine 4-pyridylamide (II) (1.25 g) obtained in Example 25 above compound (II) (1.25 g) was allowed to react with 4N-hydrogen chloride/1,4-dioxane (12 ml) to obtain 3-benzyloxy-DL-phenylalanine 4-pyridylamide dihydrochloride (II). The above compound (II) was suspended in N,N-dimethylformamide (10 ml) - tetrahydrofuran (10 ml) dry solution, and triethylamine (0.8 ml) and trans-4-(t-butyloxycarbonyl)aminomethylcyclohexylcarboxylic acid mixed acid anhydride obtained in Examples 4, 5, and 7 were added under ice-cooling, followed by stirring for 30 minutes. Further, the reaction was carried out at room temperature for 3 hours. After a conventional post-treatment, N-[trans-4-(t-butoxycarbonyl)aminomethylcyclohexylcarbonyl]-3-benzyloxy-DL-phenylalanine 4-pyridylamide (III) (1.31 g) was obtained. The above compound (IV) (1.31 g), palladium black (0.10 g), and cyclohexene (2 ml) in ethanol were stirred under ethanol reflux for 1 hour. After cooling, the solid was filtered off and the filtrate was concentrated in vacuo to obtain N-[trans-4-(t-butoxycarbonyl)aminomethylcyclohexylcarbonyl]-3-hydroxy-DL-phenylalanine 4-pyridylamide (IV) (1.10 g).

The compound (IV) (1.09 g) was dissolved in dry 1,4-dioxane (5 ml) and a 4N-hydrogen chloride/1,4- dioxane solution (15 ml) then added, followed by stirring at room temperature. After one hour, the precipitated crystal was recovered by filtration and was thoroughly washed with diethyl ether. After drying in vacuo, N-(trans-4-aminomethylcyclohexylcarbonyl)-3-hydroxy-DL-phenylalanine 4-pyridylamide dihydrochloride (0.98 g) was obtained in the form of hygroscopic white powder.

EXAMPLE 28

Synthesis of N-(trans-4-aminomethylcyclohexylcarbonyl)-3-amino-DL-phenylalanine 4-benzoylanilide hydrochloride (Compound No. 53)

N-[trans-4-(t-butoxycarbonyl)aminomethylcyclohexylcarbonyl]-3-nitro-DL-phenylalanine 4-benzoylanilide (0.60 g) obtained in Example 21 was dissolved in ethanol and 10% palladium-carbon (30 mg) was then added. While gaseous hydrogen was blown, the reaction was carried out at 60° C. for 1 hour with stirring. The palladium-carbon was filtered off and the filtrate was concentrated in vacuo to obtain N-[trans-4-(t-butoxycarbonyl)aminomethylcyclohexylcarbonyl]-3-amino-DL-phenylalanine 4-benzoylanilide (I) (0.51 g) in the form of a pale yellow powder.

To the compound (I) (0.31 g), a 4N-hydrogen chloride/1,4-dioxane solution (1.0 ml) was added under ice-cooling, followed by stirring at room temperature for 30 minutes. To this solution, diethyl ether (20 ml) was added and the precipitated crystalline substance was recovered by filtration. After drying, N-(trans-4-aminomethylcyclohexylcarbonyl)-3-amino-DL-phenylalanine -benzoylanilide dihydrochloride (II) (0.26 g) was obtained in the form of a yellow powder.

EXAMPLE 29

Synthesis of N-(4-guanidinobutyryl)-3-phenoxy-DL-phenylalanine 4-(2-methoxycarbonylvinyl)anilide methane sulfonate (Compound No. 54)

Methyl 4-aminocinnamate hydrochloride (0.41 g) and N-(t-butoxycarbonyl)-3-phenoxy-DL-phenylalanine (0.68 g) were dissolved in N,N-dimethylformamide (20 ml) and triethylamine (0.3 g) and the condensation agent, N,N-dicyclohexylcarbodiimide (0.5 g) were then added, followed by stirring at room temperature for 12 hours. After the reaction, the solvent was distilled off and the residue was extracted with dichloromethane, followed by washing with water, alkaline water, and acidic water. The extract was then dried over anhydrous sodium sulfate. The solvent was distilled off, the residue was recrystallized from ethanol to obtain pale brown N-(t-butoxycarbonyl)-3-phenoxy-DL-phenylalanine 4-(2-methoxycarbonylvinyl)anilide (I) (0.87 g), which was confirmed by IR and NMR spectrum analyses.

The compound (I) (0.7 g) was added to a 4N-hydrogen chloride/1,4-dioxane solution (5 ml), followed by stirring under ice-cooling for 30 minutes. After the reaction, diethyl ether was added and the precipitated substance was washed with diethyl ether several times to obtain 3-phenoxy-DL-phenylalanine 4-(2-methoxycarbonylvinyl)anilide hydrochloride (II) (0.57 g) in the form of a pale brown solid, which was confirmed by IR and NMR spectrum analyses.

The compound (II) (0.29 g) and 4-guanidinobutyric acid (0.1 g) were dissolved in a dry pyridine-dichloromethane mixed solvent (30 ml) and the condensation agent, 1-ethyl-3-(3-dimethylaminopropyl)carbodiimide hydrochloride (0.16 g) was then added, followed by stirring at room temperature for 12 hours. After the reaction, the solvent was distilled off, the residue was washed several times with saturated aqueous sodium bicarbonate to obtain pale brown N-(4-guanidinobutyryl)-3-phenoxy-DL-phenylalanine 4-(2-methoxycarbonylvinyl)anilide carbonate (III) (0.3 g).

The compound (III) (0.3 g) was dissolved in methanol (5 ml) and methanesulfonic acid (0.06 g) was added, followed by allowing to stand for 30 minutes. Thereafter, diethyl ether was added and the precipitated solid was washed with diethyl ether several times. Thus, N-(4-guanidinobutyryl)-3-phenoxy-DL-phenylalanine 4-(2-methoxycarbonylvinyl)anilide methane sulfonate (0.28 g) was obtained in the form of a pale brown solid.

EXAMPLE 30

Synthesis of N-(4-amidinobenzoyl)-3-phenoxy-DL-phenylalanine anilide hydroiodide (Compound No. 55)

A mixed acid anhydride prepared from cyanobenzoic acid (0.32 g) was added to 3-phenoxy-DL-phenylalanine anilide hydrochloride (0.70 g) prepared in the same manner as in Example 4, followed by stirring at room temperature for 2 hours. Thereafter, ice water (100 ml) was added, followed by extracting with ethyl acetate. The organic layer was washed with water (thrice), a 10% aqueous citric acid, water, 5% aqueous sodium bicarbonate, and a saturated aqueous sodium chloride solution, followed by drying over anhydrous sodium sulfate. After concentrating in vacuo, the precipitated crystalline substance was recovered by filtration. After recovering with diethyl ether by filtration, N-(4-cyanobenzoyl)-3-phenoxy-DL-phenylalanine anilide (I) (0.66 g), which was confirmed by an NMR spectrum analysis, was obtained in the form of pale brown powder.

The compound (I) (0.46 g) was dissolved in pyridine (1.5 ml) and triethylamine (0.5 ml) and, under ice-cooling, the solution was vigorously stirred under a hydrogen sulfide stream for one hour. This mixture was allowed to stand at room temperature for 2 days and a 10% aqueous citric acid was then added. The precipitated crystalline substance was recovered by filtration, followed by drying. Thus, yellow powder (0.42 g) was obtained. To this yellow powder (0.40 g) was suspended in acetone (50 ml) and methyl iodide (8.0 ml) was then added, followed by stirring at room temperature for 8 hours. After the solution became uniform, the solution was concentrated in vacuo and diethyl ether was added to the residue. The precipitated crystalline substance was recovered by filtration, followed by drying. Thus, white powder (0.49 g) was obtained. Furthermore, the white powder (0.45 g) was suspended in ethanol (50 ml) and anhydrous ammonium acetate (0.09 g) was then added, followed by stirring at 55° C. upon heating for 7 hours. After the reaction mixture became uniform, the reaction mixture was concentrated in vacuo. To the residue, dichloromethane and diethyl ether were added to be crystallized and the crystalline substance was recovered by filtration and was dried in vacuo. Thus, N-(4-amidinobenzoyl)-3-phenoxy-DL-phenylalanineanilide hydroiodide (0.42 g) was obtained in the form of a white powder.

EXAMPLE 31

Synthesis of
N-(trans-4-aminomethylcyclohexylcarbonyl)-3-phenoxy-DL-phenylalanine ethyl ester hydrochloride (Compound No. 57)

N-(t-butoxycarbonyl)-3-phenoxy-DL-phenylalanine (3.57 g) was dissolved in dry tetrahydrofuran (60 ml) and, under ice-cooling, triethylamine (150 ml) was then added, followed by stirring for 10 minutes. Thereafter, solution of ethyl chlorocarbonate (1.08 g) in dry tetrahydrofuran (3 ml) was added at once, followed by stirring for 30 minutes. Ethanol (1 ml) was then added, followed by stirring at room temperature for 3 hours.

After the solid substance was filtered off, the filtrate was concentrated in vacuo and the residue was extracted with ethyl acetate. The extract was washed with water and a saturated sodium chloride solution, followed by drying with anhydrous sodium sulfate. The dried extract was concentrated in vacuo to obtain N-(t-butoxycarbonyl)-3-phenoxy-DL-phenylalanine ethyl ester (I) (3.50 g), which was confirmed by an NMR spectrum analysis, in the form of a colorless oil.

To the ester (I) (1.50 g), a 4N-hydrogen chloride/1,4-dioxane solution (20 ml) was added, followed by stirring at room temperature for one hour. To this solution, hexane (200 ml) was added and the upper layer was removed by decantation. This procedure was repeated twice. The residue was dried in vacuo to obtain amorphous 3-phenoxy-DL-phenylalanine ethyl ester hydrochloride (II) (1.25 g), which was confirmed by an NMR spectrum analysis.

On the other hand, a solution of a mixed acid anhydride, in dry tetrahydrofuran, prepared from trans-4-(t-butoxycarbonyl)aminomethylcyclohexylcarboxylic acid (1.03 g), triethylamine (0.60 ml), and ethyl chlorocarbonate (0.46 g) according to the same method as in Examples 4, 5, and 7 was added to a solution of the above-mentioned hydrochloride (II) (1.25 g) in N,N-dimethylformamide (5 ml) and triethylamine (0.60 ml) was then added, followed by stirring at room temperature for 2 hours. After the solid substance was filtered off, the filtrate was concentrated in vacuo and the residue was extracted with ethyl acetate, followed by washing with water, a 10% aqueous citric acid solution, water (thrice), and a saturated aqueous sodium chloride solution, followed by drying over anhydrous sodium sulfate. After concentrating in vacuo, N-[trans-4-(t-butoxycarbonyl)aminomethylcyclohexylcarbonyl]-3-phenoxy-DL-phenylalanine ethyl ester (III) (1.62 g), which was confirmed by an NMR analysis in the form of a colorless oil.

To the compound (III) (0.60 g), a 4N-hydrogen chloride/1,4-dioxane solution (5 ml) was added, followed by stirring at room temperature for one hour. Hexane (50 ml) was then added and the upper layer was removed by decantation. This procedure was repeated twice and the residue was solidified with ethyl acetate. Thus, N-(trans-4-aminomethylcyclohexylcarbonyl)-3-phenoxy-DL-phenylalanine ethyl ester hydrochloride (0.44 g) was obtained in the form of a white powder.

EXAMPLE 32

Synthesis of
N-(trans-4-aminomethylcyclohexylcarbonyl)-3-phenoxy-DL-phenylalanine (Compound No. 58)

N-(t-butoxycarbonyl)-3-phenoxy-DL-phenylalanine (3.57 g) was dissolved in dry N,N-dimethylformamide (50 ml) and anhydrous potassium carbonate (1.38 g) was then added, followed by stirring at room temperature for 20 minutes. Thereafter, a solution of benzyl bromide (1.71 g) in dry N,N-dimethylformamide (10 ml) was added at once, followed by stirring at 45° C. upon heating for 5 hours. After cooling, the reaction mixture was poured into ice (200 g) and the separated oily substance was extracted with ethyl acetate (100 ml). The organic layer was washed with water (twice), an aqueous citric acid, water (thrice), and a saturated aqueous sodium chloride solution, followed by drying over anhydrous sodium sulfate. After concentrating in vacuo, N-(t-butoxycarbonyl)-3-phenoxy-DL-phenylalanine benzyl ester (I) (4.30 g), which was confirmed by an NMR spectrum analysis, was obtained in the form of a pale yellow oil.

To the compound (I) (2.24 g), a 4N-hydrogen chloride/1,4-dioxane solution (30 ml), followed by stirring at room temperature for one hour. To this solution, hexane (200 ml) was added and the upper layer was removed by decantation and hexane (100 ml) was further added and the upper layer was removed by decantation. The residue was dried in vacuo to obtain amorphous 3-phenoxy-DL-phenylalanine benzyl ester hydrochloride (II) (1.92 g), which was confirmed by an NMR spectrum analysis.

On the other hand, trans-4-(benzyloxycarbonyl)aminomethylcyclohexylcarboxylic acid (1.52 g) was dissolved in dry tetrahydrofuran (50 ml) and dry N,N-dimethylformamide (15 ml). Thereafter, triethylamine (0.78 ml) was added, and under ice-cooling, a solution of ethyl chlorocarbonate (0.57 g) in dry tetrahydrofuran (2 ml) was further added, followed by stirring for 20 minutes. This solution was added to the hydrochloride (II) obtained above and triethylamine (0.80 ml) was further added, followed by stirring under ice-cooling for 30 minutes and at room temperature for 3 hours. This solution was poured into ice water (200 ml) and the precipitated crystalline substance was recovered by filtration. After thoroughly washing with water and drying, N-[trans-4-(benzyloxycarbonyl)aminomethylcyclohexylcarbonyl]-3-phenoxy-DL-phenylalanine benzyl ester (III) (2.45 g), which was confirmed by an NMR spectrum analysis, was obtained in the form of a white powder.

A solution of the compound (III) (0.62 g), a palladium black (0.15 g), and cyclohexene (2 ml) in methanol (30 ml) was allowed to react under reflux of methanol for 1.5 hours. The reaction mixture was suction filtered while hot to remove the solid materials, followed by concentrating in vacuo. N-(trans-4-aminomethylcyclohexylcarbonyl)-3-phenoxy-DL-phenylalanine (0.30 g) was obtained in the form of a white powder.

EXAMPLE 33

Synthesis of
N-(trans-4-aminomethylcyclohexylcarbonyl)-3-phenoxy-DL-phenylalanine 4-pyridyl ester dihydrochloride (Compound No. 62)

To a mixture of N-(t-butoxycarbonyl)-3-phenoxy-DL-phenylalanine (1.07 g), triethylamine (0.90 ml), and 4-hydroxypyridine monohydrate (0.34 g) in acetonitrile (10 ml), 1-isopropyl-3-(3-dimethylaminopropyl)carbodiimide perchlorate (1.78 g) was added under ice-cooling, followed by stirring at room temperature for 10 hours. Ethyl acetate (50 ml) was then added followed by washing with water (twice), 1% aqueous citric acid, water, and a saturated aqueous sodium chloride solution. The reaction mixture was then dried over anhydrous sodium sulfate, followed by concentrating in vacuo. The residue was subjected to silica-gel column chromatography and, from the elute by a hexane/ethyl acetate=(2/1) solvent, N-(t-butoxycarbonyl)-3-phenoxy-DL-phenylalanine 4-pyridyl ester (I) (0.83 g), which was confirmed by an NMR spectrum analysis, was obtained in the form of colorless oil.

Following the procedure of Examples 4, 5, 7, and 31, the final compound N-(trans-4-aminomethylcyclohexylcarbonyl)-3-phenoxy-DL-phenylalanine 4-pyridyl ester dihydrochloride (II) (0.45 g) was obtained in the form of hygroscopic white powder from the compound (I).

The phenylalanine derivatives having the general formula (I) or the salts thereof according to the present invention, which are an effective component of the present proteinase inhibitor, clearly have very strong inhibition activities against either or both of kallikrein and trypsin, as shown in the following test results. It is believed that the inhibiting activity and selectivity largely depend on the substituent on 3-position of phenylalanine. That is, the 3-phenoxy-DL-phenylalanine derivatives have the strongest inhibition activity against kallikrein and, in turn, trypsin, and plasmin. On the other hand, the 3-benzoyl-DL-phenylalanine derivatives have the strongest inhibition activity against trypsin and, in turn, kallikrein, and plasmin. The effects of the 3-position substituents of phenylalanine on the inhibition activities are strengthened by the substituent A of the general formula (I). That is, when 4-guanidimobenzoyl substituent is used as the substituent A instead of trans-4-aminomethylcyclohexylcarbonyl, the larger inhibition selectivity against kallikrein can be obtained. Thus, according to the present invention, a group of the compounds having high inhibition activities and high inhibition selectivities can be provided by variously combining the substituents A, B, and X.

Furthermore, the physiological activities and various other properties of the compounds according to the present invention are remarkably improved, when compared to Aprotinin and FUT-175, which are known as pancreatitis remedy and antishocks. Thus, the present compounds are effective as pancreatitis remedies, antishocks, antiallergics, antiulcers, and immunological adjustments.

In the following, antiplasmin activity, antikallikrein activity, antitrypsin activity, antiurokinase activity and antithrombin activity of the present compounds are described in detail by referring to typical test examples.

The measurement methods employed in the following test examples are as described below. The test results are shown in Table 2 by referring to the compound Nos. in the above Table 1 for the compounds of the present invention, and the test results as well as the names and the structures of the commercially available chemicals are shown in Table 3 as Comparative Examples.

(1) Evaluation of Antiplasmin Activity (i) Determination of inhibition activity for fibrin decomposition An inhibitor sample is dissolved in a 0.18 M borate-physiological salt buffer solution (pH=7.4) to make the total volume to 600 $\mu$l. To this buffer solution, 200 $\mu$l of a 0.2% bovine fibrinogen, 100 $\mu$l of a 0.3 casein unit/ml human plasmin solution, and 100 $\mu$l of a 50 unit/ml bovine thrombin solution, all dissolved in the above-mentioned buffer, are added at a temperature of 37° C. in a constant temperature bath. Then, the dissolution time of the fibrin mass formed above is determined. Thus, the concentration $I_{50}$ of the inhibitor sample (i.e., 50% inhibition concentration, $\mu$mol), at which the dissolution time obtained in the absence of the inhibitor (i.e., about 5 minutes) is extended twice, is determined.

(ii) Determination of inhibition activity for S-2251 decomposition

An inhibitor sample is dissolved in a 0.05 M Tris-hydrochloric acid buffer solution (pH=7.4) to make the total volume to 400 $\mu$l. To this solution, 50 $\mu$l of a 3 mM S-2251 solution is added and the mixture is incubated at a temperature of 37° C. for 5 minutes in a constant temperature bath. Then, 50 $\mu$l of a 0.2 casein unit/ml human plasmin is added and the mixture is incubated at a temperature of 37° C. for 4 minutes. Thereafter, the reaction is stopped by adding 50 $\mu$l of 50% acetic acid.

The absorbance of p-nitroaniline formed in the reaction mixture is determined at 405 nm. Thus, the concentration $I_{50}$ ($\mu$mol) of the inhibitor sample, at which the absorbance is one half (i.e., $\frac{1}{2}$) of that obtained in the absence of the inhibitor, is determined.

(iii) Determination of inhibition activity for fibrinogen decomposition

An inhibitor sample is dissolved in a 0.18 M borate-physiological salt buffer solution (pH=7.4) to make the total volume to 400 $\mu$l. To this solution, 500 $\mu$l of a 0.4% bovine fibrinogen solution and 100 $\mu$l of a 1 casein unit/ml human plasmin solution, all dissolved in the above-mentioned buffer are added at a temperature of 37° C. in a constant temperature bath. After the mixture is allowed to stand at a temperature of 37° C. for 10 minutes, 3800 $\mu$l of the above-mentioned buffer containing 13.2 mM of tranexamic acid and 200 $\mu$l of a 50 unit/ml bovine thrombin solution are added to terminate the reaction. The mixture is incubated at a temperature of 37° C. for 15 minutes to form the fibrin. The fibrin clot thus formed is adhered to or wound around a glass rod and is then washed with water. The amount of the remaining fibrinogen is determined according to a tyrosine coloring method using a phenol reagent (see J. Biol. Chem., 73, 627 (1927)). From the amount of the remaining fibrinogen thus determined, the amount of decomposed fibrinogen is calculated. Thus, the concentration $I_{50}$ ($\mu$mol) of the inhibitor sample, at which the amount of decomposed fibrinogen is one half (i.e., $\frac{1}{2}$) of that obtained in the absence of the inhibitor sample, is determined.

(2) Evaluation of Antithrombin Activity (i) Determination of inhibition activity against fibrin formation An inhibitor sample is dissolved in a 0.18 M borate-physiological salt buffer solution (pH= 7.4) to make the total volume to 500 $\mu$l. To this solution, 400 $\mu$l of a 0.2% bovine fibrinogen solution and 100 $\mu$l of a 4 unit/ml bovine thrombin solution are added at a temperature of 37° C. in a constant temperature bath. Thus, a coagulation time is determined. The inhibitor concentration $I_{50}$ ($\mu$mol), at which the coagulation time obtained in the absence of the inhibitor is extended twice, is determined.

(ii) Determination of inhibition activity for S-2238 decomposition

An inhibitor sample is dissolved in a 0.05 M Tris-hydrochloric acid buffer solution (pH=8.3) to make a total volume of 400 μl. To this solution, 50 μl of a 0.2 mM S-2238 solution is added and the mixture is incubated at a temperature of 37° C. for 5 minutes in a constant temperature bath. Then, 50 μl of a 0.2 unit/ml bovine thrombin solution is added thereto and the absorbance, at 405 nm, of the p-nitroaniline formed per minute is determined at a temperature of 37° C. by using the so-called initial velocity method. Thus, the concentration $I_{50}$ (μmol) of the inhibitor sample at which the absorbance is one half (i.e., ½) of that obtained in the absence of the inhibitor sample, is determined.

(3) Evaluation of Antitrypsin Activity

Determination of inhibition activity against S-2238 decomposition

An inhibitor sample is dissolved in a 0.05 M Tris-imidazole buffer solution (pH=8.1) and 125 μl of a 1 mM S-2238 solution is added to make the total volume to 1.20 ml. The mixture is incubated at a temperature of 37° C. for 5 minutes in a constant temperature bath. To this mixture, 0.05 ml of bovine trypsin is added and the absorbance, at 405 nm, of the p-nitroaniline formed per minute is determined at a temperature of 37° C. by using the so-called initial velocity method. Thus, the concentration $I_{50}$ (μmol) of a inhibitor sample, at which the absorbance is one half (i.e., ½) of that obtained in the absence of the inhibitor sample, is determined.

(4) Evaluation of Anti-Plasma Kallikrein Activity

Determination of inhibition activity for S-2302 decomposition

An inhibitor sample is dissolved in a 0.05 M Tris-hydrochloric acid buffer solution (pH=7.8) to make the total volume to 400 μl. To this solution, 50 μl of a 2 mM S-2302 solution is added and the mixture is incubated at a temperature of 37° C. for 5 minutes in a constant temperature bath. Then, 50 μl of a 0.12 unit/ml human plasma kallikrein is added and the mixture is incubated at a temperature of 37° C. for 5 minutes. Thereafter, 50 μl of 50% acetic acid is added to terminate the reaction. The absorbance of the p-nitroaniline formed in the reaction mixture is measured at 405 nm. Thus, the concentration $I_{50}$ (μmol) of the inhibitor sample, at which the absorbance is one half (i.e., ½) of that obtained in the absence of the inhibitor sample, is determined.

(5) Evaluation of Antiurokinase Activity

Determination of inhibition activity for S-2444 decomposition

An inhibitor sample is dissolved in a 0.05 M Tris-hydrochloric acid buffer solution (pH=8.8) to make the total volume to 400 μl. To this solution, 50 μl of a 1 mM S-2444 solution is added and the mixture is incubated at a temperature of 37° C. for 5 minutes in a constant temperature bath. Then, 50 μl of a 500 unit/ml human urokinase is added and the mixture is incubated at a temperature of 37° C. for 5 minutes. Thereafter, 50 μl of 50% acetic acid is added to terminate the reaction. The absorbance of the p-nitroaniline formed in the reaction mixture is measured at 405 nm. Thus, the concentration $I_{50}$ (μmol) of the inhibitor sample, at which the absorbance is one half (i.e., ½) of that obtained in the absence of the inhibitor sample, is determined.

When the compounds of the present invention are used as a medicine, there are no critical limitations to the administration methods. The present proteinase inhibitor can be formulated by any conventional method in pharmaceutics. For example, the present proteinase inhibitor may be applied in any conventional manner including intravenous injection, intramuscular injection, instillation, oral administration, respiratory inhalation, instillation, rhinenchysis, and external skin treatment. Although there are no critical limitations to the administration dosage, the suitable dosage is 100 to 1000 mg/day/person, which can be conveniently decreased or increased as desired, as a matter of course.

TABLE 2

| Compound No. | Plasmin S-2251 | Plasmin Fibrin | Thrombin S-2238 | Thrombin Fibrinogen | Trypsin S-2238 | Plasma Kallikrein S-2302 | Urokinase S-2444 |
|---|---|---|---|---|---|---|---|
| 1 | 46 | 15 | | >100 | 15 | 1.3 | >100 |
| 2 | 19 | 14 | >100 | >100 | 2.3 | 0.38 | 110 |
| 3 | 31 | 11 | | >100 | 2.3 | 1.2 | >100 |
| 4 | >100 | >50 | | >50 | >150 | >100 | >200 |
| 5 | 22 | 12 | | >100 | 2.5 | 8.7 | 38 |
| 6 | 360 | 190 | | >500 | >15 | 11 | >500 |
| 7 | 98 | 70 | | >1000 | 15 | 2 | 250 |
| 8 | 65 | 24 | >100 | >400 | 8.8 | 0.83 | 87 |
| 9 | 31 | 10 | >1000 | >500 | 2.3 | 0.43 | 190 |
| 10 | | | | >125 | >150 | >250 | >250 |
| 11 | 610 | 220 | | | 68 | 190 | >400 |
| 12 | 1000 | 130 | | >1000 | >150 | 55 | >1000 |
| 13 | | | | >100 | >150 | >200 | >200 |
| 14 | 940 | 340 | | >500 | 100 | 340 | >500 |
| 15 | >100 | >100 | | >100 | >150 | >200 | >100 |
| 16 | >1000 | >1000 | | >1000 | >150 | >1000 | >500 |
| 17 | 1000 | 570 | | >1000 | >150 | >1000 | >500 |
| 18 | 430 | >100 | | >100 | >150 | >500 | >1000 |
| 19 | >1000 | >1000 | | >1000 | >150 | >1000 | >1000 |
| 20 | >100 | >60 | | >1000 | >150 | >1000 | >1000 |
| 21 | 320 | 150 | | >200 | >150 | >400 | >1000 |
| 22 | >1000 | >500 | | >500 | >150 | >500 | |
| 23 | 750 | 620 | | >1000 | 8.2 | 350 | >500 |
| 24 | >1000 | 700 | | >1000 | >150 | >1000 | >1000 |
| 25 | 490 | 450 | | >1000 | >150 | 500 | >1000 |
| 26 | >1000 | 400 | | >1000 | >150 | >1000 | >1000 |
| 27 | 280 | 440 | | >1000 | >150 | >1000 | >1000 |
| 28 | >1000 | 260 | | >1000 | 87 | >1000 | >1000 |
| 29 | >1000 | >1000 | | >1000 | >150 | >1000 | >1000 |
| 30 | >20 | >50 | | | >150 | >10 | |
| 31 | 160 | >100 | | >100 | >150 | >100 | >500 |

TABLE 2-continued

| Compound No. | Plasmin S-2251 | Plasmin Fibrin | Thrombin S-2238 | Thrombin Fibrinogen | Trypsin S-2238 | Plasma Kallikrein S-2302 | Urokinase S-2444 |
|---|---|---|---|---|---|---|---|
| 32 | 120 | >25 |  | >25 | 15 | 2.2 | 100 |
| 33 | >100 | >25 |  | >25 | 42 | 4.5 | >200 |
| 34 |  |  |  | >50 | >150 | 270 | >200 |
| 35 | >500 | >200 |  |  | 240 | >500 |  |
| 36 | 25 | >25 |  |  | 17 | 1.9 |  |
| 57 | 260 | 110 |  | >1000 | 25 | 5.7 | 350 |
| 58 |  |  | >1000 |  | >150 | 600 | >1000 |

TABLE 3

| No | Compound Name |
|---|---|
| 1 | Aprotinin |
| 2 | FUT-175 |

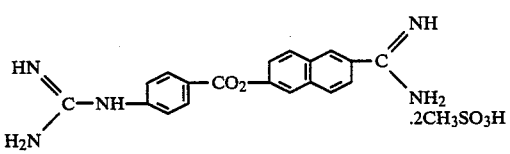
.2CH₃SO₃H

TABLE 4

| No | Compound Name | plasmin S-2251 | plasmin Fibrin | Thrombin S-2238 | Thrombin Fibrinogen | Trypsin S-2238 | Plasma Kallikrein S-2302 | Urokinase S-2444 |
|---|---|---|---|---|---|---|---|---|
| 1 | Aprotinin U/ml | 2.5 | 1.6 | >1000 | >1000 | 3.5 | 30 | >1000 |
| 2 | FUT-175 μ/mol | 0.43 | 0.22 | 5.9 | 59 | 0.27 | 0.076 | 0.013 |

We claim:

1. A phenylalanine derivative having the formula (I):

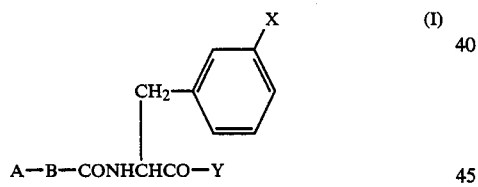

wherein

A represents

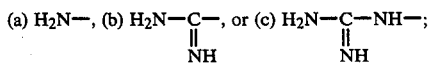

B represents

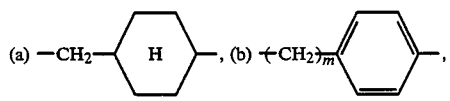

or (c) $+CH_2)_{\overline{n}}$, wherein m is 0, 1, 2 and n is 3, 4, or 5;

X represents (a) hydroxy, (b) nitro, (c) amino, (d) phenoxy which may be substituted with (i) halogen or (ii) nitro, (e) $C_1$-$C_4$ alkyloxy which may be substituted with (i) phenyl or (ii) benzoyl, (f) benzoyl, (g) pyridyloxy which may be substituted with (i) halogen or (ii) nitro, or (h) $C_1$-$C_4$ alkyl which may be substituted with halogen;

Y represents

or —$OR^3$ wherein $R^1$ and $R^2$ are independently (a) hydrogen, (b) phenyl which, may be substituted with (i) benzoyl, (i) $C_1$-$C_4$ alkylcarbonyl, (iii) $C_1$-$C_4$ alkyl which may be further substituted with $C_1$-$C_4$ alkoxycarbonyl or hydroxycarbonyl, (iv) $C_2$-$C_5$ alkenyl which may be further substituted with hydroxycarbonyl or $C_1$-$C_4$ alkoxycarbonyl, (v) $C_1$-$C_4$ alkoxycarbonl, or (vi) amidino, (c) pyridyl which may be substituted with halogen or carboxyl (d) imidazolyl, (e) pyrimidyl, (f) tetrazolyl, (g) thiazolyl which may be substituted with $C_1$-$C_4$ alkyl which may be further substituted with $C_1$-$C_4$ alkoxycarbonyl, (h) $C_1$-$C_6$ alkyl which may be substituted with $C_1$-$C_4$ alkoxy, $C_1$-$C_4$ alkoxycarbonyl, phenyl, or benzoyl, (i) $C_5$-$C_7$ cycloalkyl which may be substituted with $C_1$-$C_4$ alkoxycarbonyl or (j) $R^1$ and $R^2$ may form, with the nitrogen atom attached thereto, (i) piperazyl which may be substituted on the nitrogen atom with $C_1$-$C_4$ alkyl which may be further substituted with phenyl, (ii) piperidino which may be substituted with carboxyl or $C_1$-$C_4$ alkoxycarbonyl, (iii) pyrrolidyl which may be substituted with $C_1$-$C_4$ alkoxycarbonyl, or (iv) morpholyl; and $R^3$ represents (a) hydrogen, (b) $C_1$-$C_6$ alkyl which may be substituted with (i) $C_1$-$C_4$ alkoxy, (ii) phenyl, or (iii) pyridyl, or (c) pyridyl; or a pharmaceutically acceptable salt thereof.

2. A phenylalanine derivative as claimed in claim 1, wherein the pharmaceutically acceptable salt is at least one acid salt selected from the group consisting of hydrochloride, hydrobromide, hydroiodide, sulfate, nitrate, phosphate, oxalate, succinate, glycolate, malate, citrate, lactate, benzene sulfonate, toluene sulfonate, and methane sulfonate.

3. A proteinase inhibitor composition comprising as an essential component a therapeutically effective amount of the phenylalanine derivative of claim 1 or the pharmaceutically acceptable salt thereof and a pharamaceutically acceptable carrier.

4. A proteinase inhibitor composition as claimed in claim 3, wherein the pharmaceutically acceptable salt is at least one salt selected from the group consisting of hydrochloride, hydrobromide, hydroiodide, sulfate, nitrate, phosphate, oxalate, succinate, glycolate, malate, citrate, lactate, benzene sulfonate, toluene sulfonate, and methane sulfonate.

5. A phenylalanine derivative as claimed in claim 1, wherein A and B in the formula (I) represent as its combination,

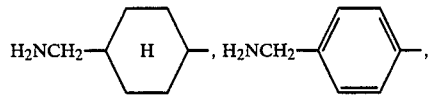

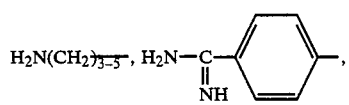

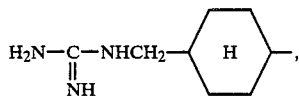

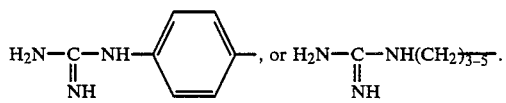

6. A phenylalanine derivative as claimed in claim 1, wherein A and B in the formula (I) represent as its combination,

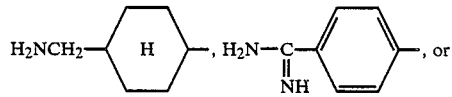

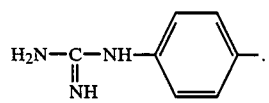

7. A phenylalanine derivative as claimed in claim 1, wherein in the formula (I), A and B represent as its combination

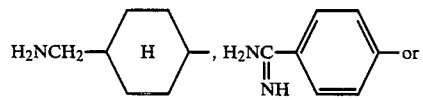

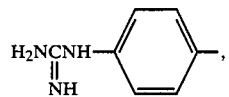

X represents nitro; phenoxy which may be substituted with halogen or nitro; $C_1$ alkyloxy which may be substituted with benzoyl; benzoyl; pyridyloxy which may be substituted with halogen or nitro, and Y represents NHR or $OR_4$ wherein R is (a) phenyl which may be substituted with (i) benzoyl, (ii) $C_1$-$C_4$ alkylcarbonyl, (iii) $C_1$-$C_3$ alkyl which may be further substituted with $C_1$-$C_2$ alkoxycarbonyl, (b) pyridyl which may be substituted with halogen or carboxyl, (c) tetrazolyl, (d) thiazolyl which may be substituted with $C_1$-$C_3$ alkyl which may be further substituted with $C_1$-$C_2$ alkoxycarbonyl, (e) $C_1$-$C_4$ alkyl which may be substituted with $C_1$-$C_2$ alkoxy, $C_1$-$C_2$ alkoxycarbonyl, or (f) cyclohexyl which may be substituted with $C_1$-$C_2$ alkoxycarbonyl, and $R_4$ is $C_1$-$C_4$ alkyl which may be substituted with $C_1$-$C_2$ alkoxy, or pyridyl, or pyridyl; or a pharmaceutically acceptable salt thereof.

8. A proteinase inhibitor composition comprising as an essential component a therapeutically effective amount of the phenylalanine derivative of claim 7 or the pharmaceutically acceptable salt thereof and a pharmaceutically acceptable carrier.

9. N-(trans-4-aminomethylcyclohexylcarbonyl)-3-phenoxy-DL-phenylalanine 4-acetylanilide or its salts.

10. N-(trans-4-aminomethylcyclohexylcarbonyl)-3-phenoxy-DL-phenylalanine 4-pyridylamide or its salts.

11. N-(trans-4-aminomethylcyclohexylcarbonyl}-3-phenoxy-DL-phenylalanine 2-(4-ethoxycarbonyl)-thiazolylamide or its salts.

12. N-(trans-4-aminomethylcyclohexylcarbonyl)-3-phenoxy-DL-phenylalanine 2(methoxy)ethyl ester or its salts.

13. N-(trans-4-aminomethylcyclohexylcarbonyl)-3-phenoxy-DL-phenylalanine 3-pyridylmethyl ester or its salts.

14. N-(trans-4-aminomethylcyclohexylcarbonyl)-3-(5-nitro-2-pyridyloxy)-DL-phenylalanine 4-acetylanilide or its salts.

15. N-(trans-4-aminomethylcyclohexylcarbonyl)-3-benzoyl-DL-phenylalanine 3-methoxypropylamide or its salts.

16. N-(trans-4-aminomethylcyclohexylcarbonyl)-3-benzoyl-DL-phenylalanine 4-benzoylanilide or its salts.

17. N-(4-guanidinobenzoyl)-3-phenoxy-DL-phenylalanine 4-hydroxycarbonylmethylanilide or its salts.

18. N-(4-amidinobenzoyl)-3-phenoxy-DL-phenylalanine anilide or its salts.

19. N-(trans-4-aminomethylcyclohexylcarbonyl)-3-(3-chloro-2-nitro)phenoxy-DL-phenylalanine 4-pyridylamide or its salts.

20. N-(trans-4-aminomethylcyclohexylcarbonyl)-3-phenoxy-DL-phenylalanine 2-chloro-4-pyridylamide, or its salts.

* * * * *